US009322012B2

(12) United States Patent
Dasgupta et al.

(10) Patent No.: US 9,322,012 B2

(45) Date of Patent: Apr. 26, 2016

(54) ENZYME COMPOSITIONS

(71) Applicant: University of Calcutta, Kolkata, West Bengal (IN)

(72) Inventors: Anjan Kr. Dasgupta, Kolkata (IN); Tamoghna Bhattacharyya, Dist-Birbhum (IN); Arka Mukhopadhyay, Howrah (IN); Nalok Dutta, Kolkata (IN); Krishanu Chakraborty, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 0 days.

(21) Appl. No.: 14/455,780

(22) Filed: Aug. 8, 2014

(65) Prior Publication Data

US 2015/0079656 A1 Mar. 19, 2015

(30) Foreign Application Priority Data

Aug. 9, 2013 (IN) ............................ 941/KOL/2013

(51) Int. Cl.
*C12N 11/04* (2006.01)
*C12N 13/00* (2006.01)
*C12N 9/96* (2006.01)

(52) U.S. Cl.
CPC *C12N 11/04* (2013.01); *C12N 9/96* (2013.01); *C12N 13/00* (2013.01)

(58) Field of Classification Search
None
See application file for complete search history.

(56) References Cited

U.S. PATENT DOCUMENTS

2010/0215724 A1 8/2010 Prakash et al.
2011/0263514 A1* 10/2011 Rana ........................... 514/20.9
2015/0044710 A1* 2/2015 Dasgupta et al. ................ 435/8

FOREIGN PATENT DOCUMENTS

WO WO-2013/175259 A1 11/2013

OTHER PUBLICATIONS

Bhattacharyya T. et al. Reusable Glucose Sensing Using Carbon Nanotube Based Self Assembly. Nanoscale 5(19)9231-9237, Oct. 7, 2013.*

Yan, Y. et al. Multi-Walled Carbon Nanotube Based Glucose/O2 Biofuel Cell with Glucose Oxidase and Laccase as Biocatalysts 7(4/5)1625-1630, Apr./May 2007.*

Caseli L. et al. High Enzymatic Activity Preservation with Carbon Nanotubes . . . Langmuir 28(12)5398-5403, Mar. 27, 2012.*

Liu Y. et al. Enzyme Immobilization and Direct Electrochemistry Based on a New Matrix of Phospholipid Monolayer Functionalized Graphene. Chemistry An Asian J 7(12)2824-2829, Dec. 2012.*

Abadulla, E. et al., "Decolorization and Detoxification of Textile Dyes with a Laccase from Trametes hirsute," Applied and Environmental Microbiology, vol. 66, Issue 8, pp. 3357-3362 (2000).

Adinarayana et al., "Purification and Partial Characterization of Thermostable Serine Alkaline Protease from a Newly Isolated Bacillus subtilis PE-11," AAPS PharmSciTech, 4 (4), 2003, 9 pages.

Adinew, B., "Textile Effluent Treatment and Decolorization Techniques—a Review," Chemistry: Bulgarian Journal of Science Education, vol. 21 No. 3, pp. 434-465 (2012).

Allen, S. J. et al., "Electro oxidation of dyestuffs in waste waters," Journal of Chemical Technology and Biotechnology, vol. 62, Issue 2, pp. 111-117 (1995).

Beek, T. A. V. et al., "Fungal bio-treatment of spruce wood with Trametes versicolor for pitch control: influence on extractive contents, pulping process parameters, paper quality and effluent toxicity," Bioresource Technology, vol. 98, pp. 302-311 (2007).

Bhattacharyya, T., et al., "Molecular discriminators using single wall carbon nanotubes," Nanotechnology, vol. 23, No. 38, pp. 1-8 (2012).

Blanquez, P. et al., "Mechanism of textile metal dye biotransformation by Trametes versicolor," Water Research, vol. 38 pp. 2166-2172 (2004).

Cavicchioli, R. et al., "Low-temperature extremophiles and their applications," Current Opinion in Biotechnology, vol. 13, Issue 3, pp. 253-261 (2002).

Chandra, R. P. and Ragauskas A. J., "Evaluating laccase-facilitated coupling of phenolic acids to high-yield Kraft pulps," Enzyme and Microbial Technology, vol. 30, Issue 7, pp. 855-861 (2002).

Chesson, A., "A Review: Maceration in Relation to the Post-harvest Handling and Processing of Plant Material," Journal of Applied Bacteriology, vol. 48, Issue 1, pp. 1-45 (1980).

Demirjian, D. C. et al., "Enzymes from extremophiles," Current Opinion in Chemical Biology , vol. 5, Issue 2, pp. 144-151 (2001).

Feller, G. and Gerday C., "Psychrophilic Enzymes: Hot Topics in Cold Adaptation," Nature Review, Microbiology, vol. 1, pp. 200-208 (2003).

Gerday, C. et al., "Cold-adapted enzymes: from fundamentals to biotechnology," Trends Biotechnology, vol. 18, pp. 103-107 (2000).

Gupta, R. et al., "Bacterial alkaline proteases: molecular approaches and industrial applications," Appl Microbiol Biotechnol, vol. 59, pp. 15-32 (2002).

Horikoshi, K., "Enzymes of alkalophiles," In: Fogarty, W. M., Kelly, C. T. (Eds.), Microbial Enzymes and Biotechnology, second ed. Elsevier Applied Science, London, pp. 275-294 (1990).

Hou, H. et. al., "Enhancement of laccase production by Pleurotus ostreatus and its use for the decolorization of anthraquinone dye," Process Biochemistry, vol. 39, Issue 11, pp. 1415-1419 (2004).

Huston, A. L., "Biotechnological Aspects of Cold-Adapted Enzymes," Psycrhophilic: from Biodiversity to Biotechnology, Springer-Verlag Berlin Heidelberg, pp. 347-363 (2008).

Huttermann, A. et al., "Modification of lignin for the production of new compounded materials," Applied Microbiology and Biotechnology, vol. 55, Issue 4, 387-394 (2001).

Kashyap et al., "Applications of pectinases in the commercial sector: a review," Bioresource Technology, 77, pp. 215-227 (2001).

Laing, I. G., "The Impact of Effluent Regulations on the Dyeing Industry," Review of Progress in Coloration, vol. 21, 56-71 (1991).

Lund, M. and Ragauskas, A., "Enzymatic modification of Kraft lignin through oxidative coupling with water-soluble phenols," Applied Microbiology and Biotechnology, vol. 55, Issue 6, pp. 699-703 (2001).

(Continued)

*Primary Examiner* — Ralph Gitomer

(74) *Attorney, Agent, or Firm* — Foley & Lardner LLP

(57) ABSTRACT

The present technology provides for enzyme compositions with enhanced enzyme activity, thermophilic and psychrophilic stability.

11 Claims, 19 Drawing Sheets

(56) References Cited

OTHER PUBLICATIONS

Milstein, O. et al., "Removal of chlorophenols and chlorolignins from bleaching effluent by combined chemical and biological treatment," Water Science & Technology, vol. 20, No. 1, pp. 161-170 (1988).
Mukhopadhyay, A. et al., "Improvement of thermostability and activity of pectate lyase in the presence of hydroxyapatite nanoparticles," Bioresource Technology, vol. 116, pp. 348-354 (2012).
Mukhopadhyay, A. et al., "Thermostability, pH stability and dye degrading activity of a bacterial laccase are enhanced in the presence of Cu2O nanoparticles," Bioresource Technology, vol. 127, pp. 25-36 (2013).
Othman et al., "Recovery of synthetic dye from simulated wastewater using emulsion liquid membrane process containing tridodecyl amine as a mobile carrier," Journal of Hazardous Materials, 198, pp. 103-112 (2011).
Pearce, C. I. et al., "The removal of colour from textile wastewater using whole bacterial cells: a review," Dyes and Pigments, vol. 58, pp. 179-196 (2003).
Pereira, L. et al., "Environmentally friendly bleaching of cotton using laccases," Environ. Chem. Lett., vol. 3, pp. 66-69 (2005).
Ragauskas et al., "From wood to fuels—Integrating biofuels and pulp production," Industrial Biotechnology, vol. 2, No. 1, pp. 55-65 (2006).
Reid, I. and Ricard, M., "Pectinase in papermaking: solving retention problems in mechanical pulps bleached with hydrogen peroxide," Enzyme and Microbial Technology, vol. 26, Issues 2-4, pp. 115-123 (2000).
Russell, N. J., "Molecular adaptations in psychrophilic bacteria: Potential for biotechnological applications," Adv. Biochem. Eng. Biotechnol, vol. 61, pp. 1-21 (1998).
Salony et al., "Production and characterization of laccase from Cyathus bulleri and its use in decolourization of recalcitrant textile dyes," Appl. Microbiol. Biotechnol, vol. 71, Issue 5, pp. 646-653 (2006).
Siddiqui, K. S. et al., "Thermodynamic activation properties of elongation factor 2 (EF-2) proteins from psychrotolerant and thermophilic Archaea," Extremophiles, vol. 6, Issue 2, pp. 143-150 (2002).
Singh, G.P.B. et al., "Carbon Nanotubes—A Novel Drug Delivery System," International Journal of Research in Pharmacy and Chemistry, vol. 2, No. 2, pp. 523-532 (2012).
Thornton, J. et al., "Polysaccharides Dissolved from Norway Spruce in Thermomechanical Pulping and Peroxide Bleaching," Journal of Wood Chemistry and Technology, vol. 14, Issue 2, pp. 159-175 (1994).
Trytek, M. and Fiedurek, J., "A novel psychrotrophic fungus, Mortierella minutissima, for D-limonene biotransformation," Biotechnol Lett., vol. 27, Issue 3, pp. 149-153 (2005).
Tzanov, T. et al., "Effect of Some Process Parameters in Enzymatic Dyeing of Wool," Applied Biochemistry and Biotechnology, vol. 111, Issue 1, pp. 1-13 (2003).
Vermelho, A. B. et al., "Microbial Enzyme: Applications in Industry and in Bioremediation," Enzyme Research, vol. 2012, pp. 1-2 (2012).
Viswanath et al., "Fungal Laccases and Their Applications in Bioremediation," Enzyme Research, May 15, 2014, 21 pages.

* cited by examiner

Pectinase at 4°C

Pectinase at 80°C

Laccase at 4°C

Laccase at 80°C

Protease at 4°C

Protease at 80°C

Cellulase at 4°C

Cellulase at 80°C

Xylanase at 4°

Xylanase at 80°C

Pectinase at 4°C

Pectinase at 80°C

Laccase at 4°C

Laccase at 80°C

Protease at 4°C

Protease at 80°C

Cellulase at 4°C

Cellulase at 80°C

Xylanase at 4°C

Xylanase at 80°C

Pectinase at 4°C

Pectinase at 80°C

Laccase at 4°C

Laccase at 80°C

Protease at 4°C

Protease at 80°C

Cellulase at 4°C

Cellulase at 80°C

Xylanase at 4°C

Xylanase at 80°C

ENZYME COMPOSITIONS

CROSS-REFERENCE TO RELATED APPLICATION

The present application claims priority to Indian Patent Application No. 941/KOL/2013 filed Aug. 9, 2013, the content of which is incorporated herein by reference in its entirety.

FIELD

The present technology relates to enzyme compositions with enhanced enzyme activity and methods of making and using the same.

BACKGROUND

The following description is provided to assist the understanding of the reader. None of the information provided or references cited is admitted to be prior art to the present invention.

The bio-catalytic uses for enzymes has grown immensely in recent years since they are ecologically correct, have a high specificity, present chemo-regio-enantio selectivity, and have a wide diversity of reactions. Moreover, the conditions to obtain and optimize the production of enzymes in terms of nutrients, pH, temperature, and aeration are easily controlled in bioreactors.

The industrial application of enzymes that can withstand harsh conditions has greatly increased over the past decade. This is mainly a result of the discovery of novel enzymes from extremophilic microorganisms.

SUMMARY

The present technology relates generally to entrapping enzymes in lipid-functionalized graphenes, lipid-functionalized fullerenes, or lipid-functionalized carbon nanotubes to enhance the enzyme's activity. In some embodiments, nanoparticles are entrapped with the enzyme in the lipid-functionalized graphenes, lipid-functionalized fullerenes, or lipid-functionalized carbon nanotubes.

In one aspect, the present technology provides an enzyme composition having one or more lipid-functionalized graphenes, lipid-functionalized fullerenes, or lipid-functionalized carbon nanotubes and at least one enzyme entrapped by, but not linked to, the lipid-functionalized graphenes, lipid-functionalized fullerenes, or lipid-functionalized carbon nanotubes, wherein the entrapped enzyme in the composition has an enhanced activity as compared to a control enzyme.

In one aspect, the present technology provides a method for entrapping an enzyme. In some embodiments the method includes contacting lipid-functionalized graphenes, lipid-functionalized fullerenes, or lipid-functionalized carbon nanotubes and at least one enzyme in a mixture under conditions suitable to entrap the enzyme in the lipid-functionalized graphenes, lipid-functionalized fullerenes, or lipid-functionalized carbon nanotubes and sonicating the mixture.

In one aspect, the present technology provides for a method for treating a substrate, the method comprising, contacting a first substrate with an enzyme composition, the enzyme composition including lipid-functionalized graphenes, lipid-functionalized fullerenes, or lipid-functionalized carbon nanotubes and at least one entrapped enzyme, wherein the enzyme is entrapped by, but not linked to, the lipid-functionalized graphenes, lipid-functionalized fullerenes, or the lipid-functionalized carbon nanotubes, and wherein the entrapped enzyme in the enzyme composition has an enhanced activity as compared to a control enzyme.

In one aspect, the present technology provides for a kit. In some embodiments, the kit includes a first container with lipid-functionalized graphenes, lipid-functionalized fullerenes, or lipid-functionalized carbon nanotubes and a second container with at least one enzyme.

In one aspect, the present technology provides for a kit having an enzyme composition, wherein the enzyme composition includes lipid-functionalized graphenes, lipid-functionalized fullerenes, or lipid-functionalized carbon nanotubes and at least one enzyme entrapped by, but not linked to, the lipid-functionalized graphenes, lipid-functionalized fullerenes, or lipid-functionalized carbon nanotubes, wherein the entrapped enzyme in the composition has an enhanced activity as compared to a control enzyme.

DETAILED DESCRIPTION

Figure 1:
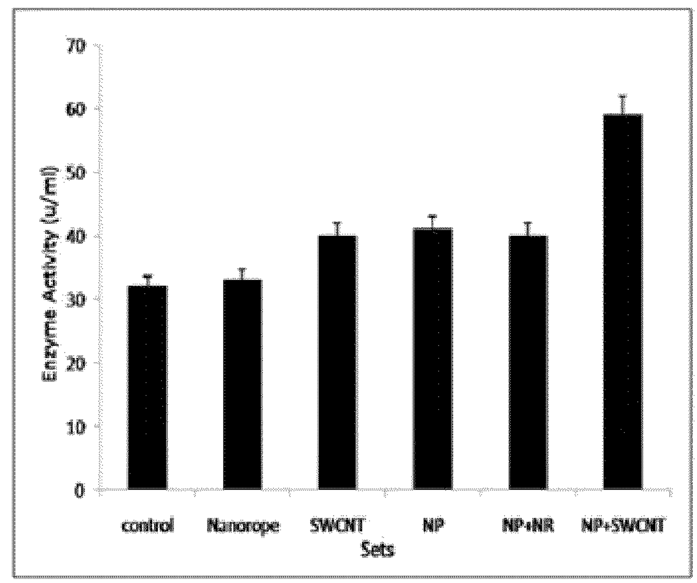
FIGS. 1A and 1B are graphs illustrating enzymatic activity of pectinase. as a pure enzyme without NP or SWCNT (control), a pectinase in combination with SWCNT without entrapment (nanorope), a pectinase in combination with SWCNT with entrapment (SWCNT), in combination with NP without SWCNT (NP), a pectinase in combination with NP and SWCNT without entrapment (NP+NR), and a pectinase in combination with NP and SWCNT with entrapment (NP+SWCNT), at 4° C. and 80° C., respectively.
Figure 1:
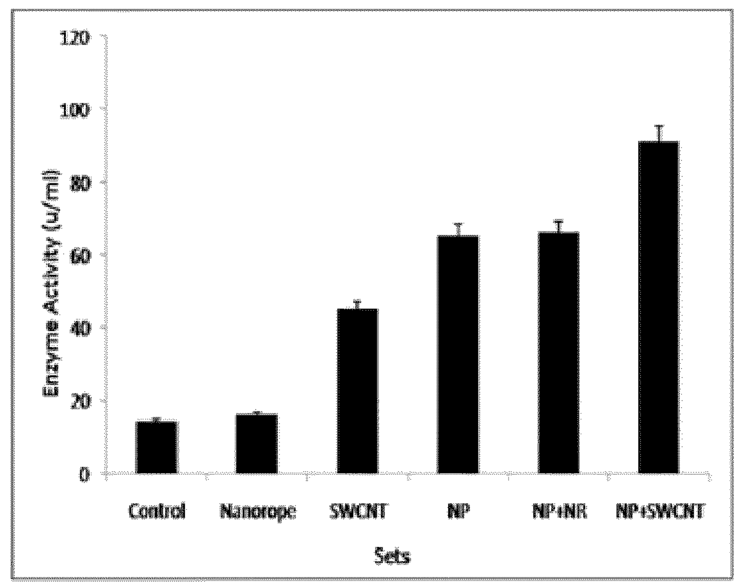
Figure 2A:
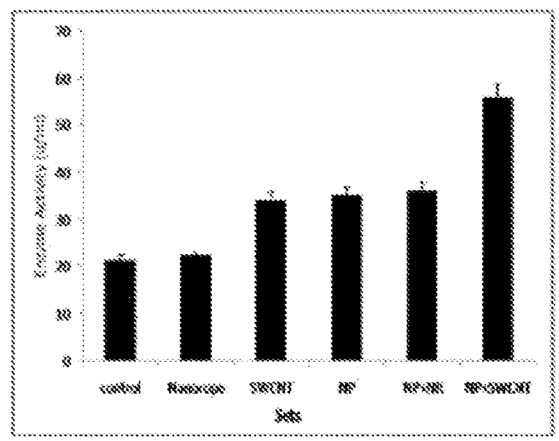
FIGS. 2A and 2B are graphs comparing the enzymatic activity of laccase as a pure enzyme without NP or SWCNT (control), a laccase in combination with SWCNT without entrapment (nanorope), a laccase in combination with SWCNT with entrapment (SWCNT), a laccase in combination with NP without SWCNT (NP), a laccase in combination with NP and SWCNT without entrapment (NP+NR), and a laccase in combination with NP and SWCNT with entrapment (NP+SWCNT), at 4° C. and 80° C., respectively.
Figure 2B:
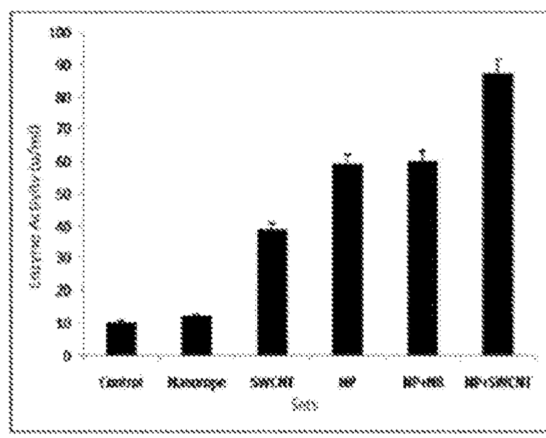
Figure 3A:
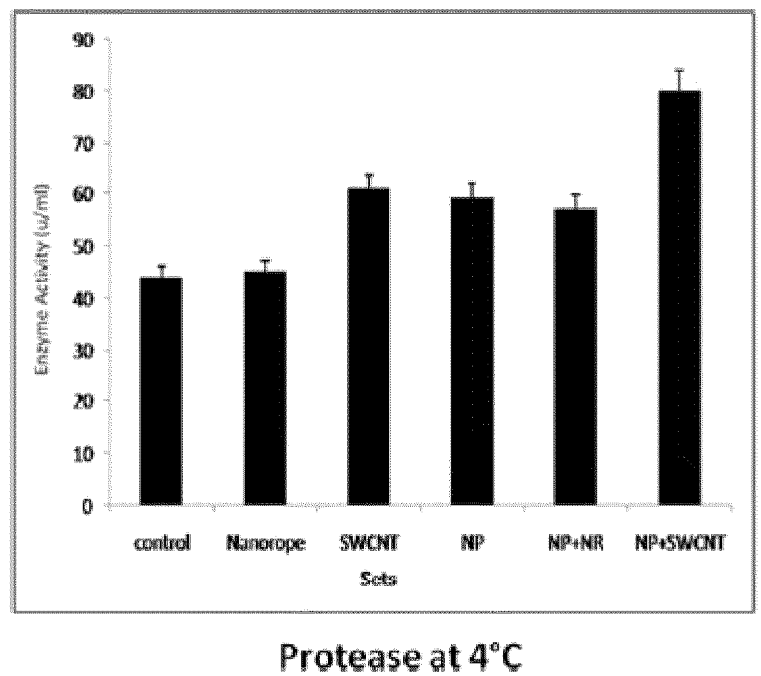
FIGS. 3A and 3B are graphs comparing the enzymatic activity of protease as a pure enzyme without NP or SWCNT (control), a protease in combination with SWCNT without entrapment (nanorope), a protease in combination with SWCNT with entrapment (SWCNT), a protease in combination with NP without SWCNT (NP), a protease in combination with NP and SWCNT without entrapment (NP+NR), and a protease in combination with NP and SWCNT with entrapment (NP+SWCNT), at 4° C. and 80° C., respectively.
Figure 3B:
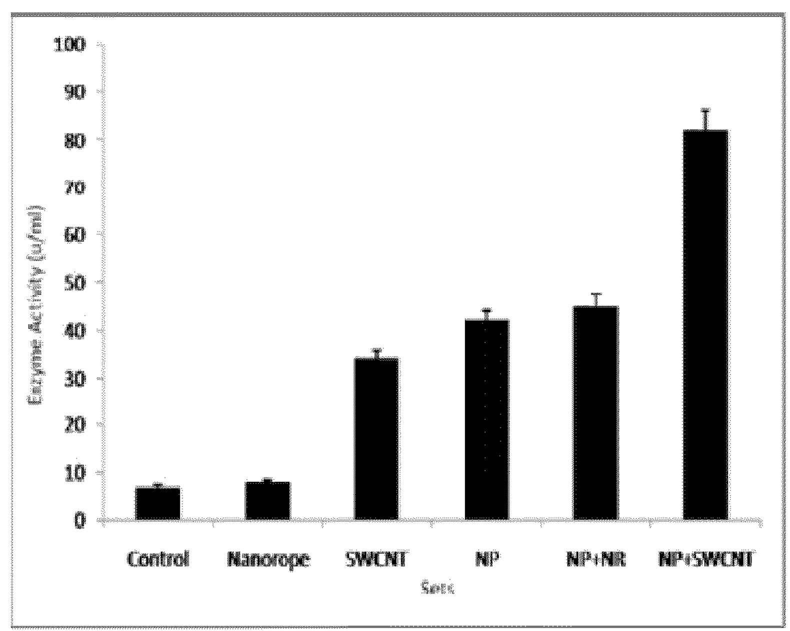
Figure 4:
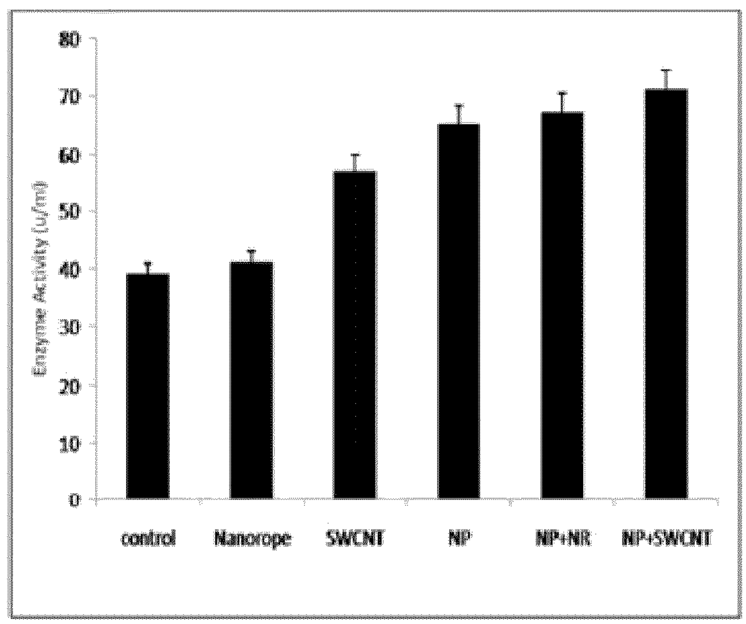
FIGS. 4A and 4B are graphs comparing the enzymatic activity of cellulase as a pure enzyme without NP or SWCNT (control), a cellulase in combination with SWCNT without entrapment (nanorope), a cellulase in combination with SWCNT with entrapment (SWCNT), a cellulase in combination with NP without SWCNT (NP), a cellulase in combination with NP and SWCNT without entrapment (NP+NR), and a cellulase in combination with NP and SWCNT with entrapment (NP+SWCNT), at 4° C. and 80° C., respectively.
Figure 4:
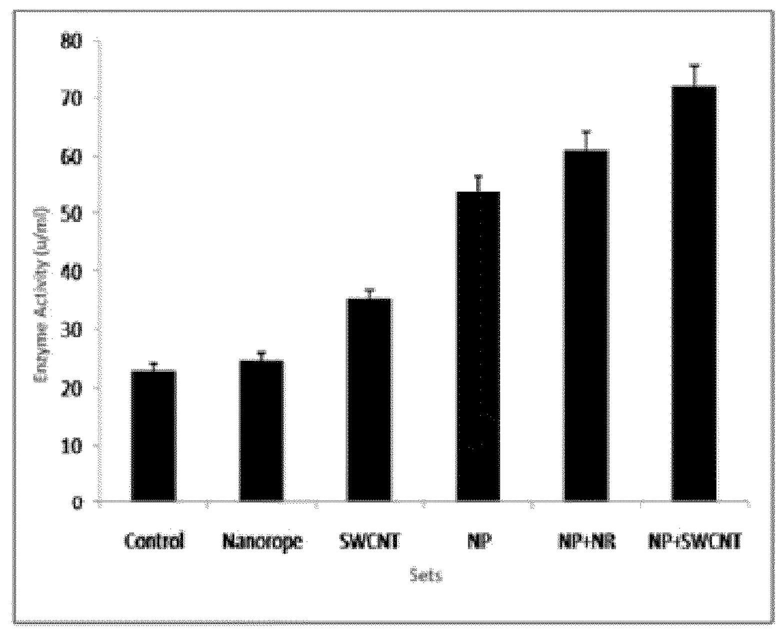
Figure 5A:
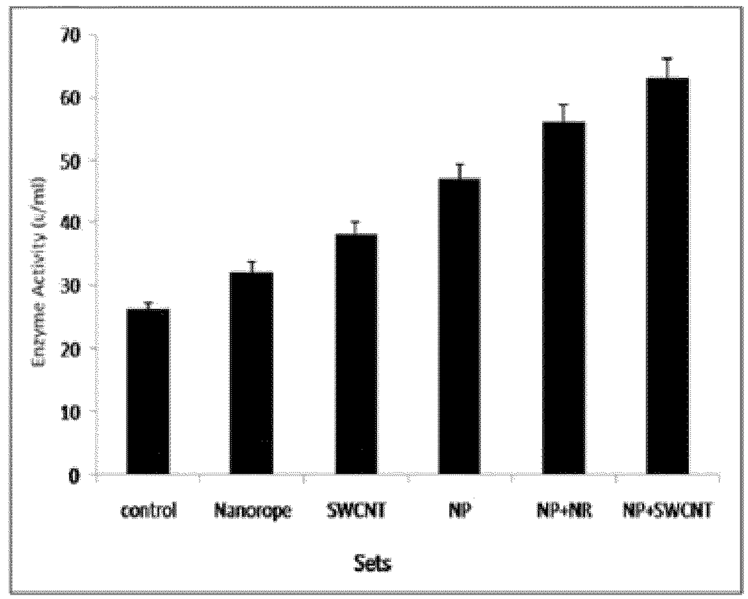
FIGS. 5A and 5B are graphs comparing the enzymatic activity of xylanase as a pure enzyme without NP or SWCNT (control), a xylanase in combination with SWCNT without entrapment (nanorope), a xylanase in combination with SWCNT with entrapment (SWCNT), a xylanase in combination with NP without SWCNT (NP), a xylanase in combination with NP and SWCNT without entrapment (NP+NR), and a xylanase in combination with NP and SWCNT with entrapment (NP+SWCNT), at 4° C. and 80° C., respectively.
Figure 5B:
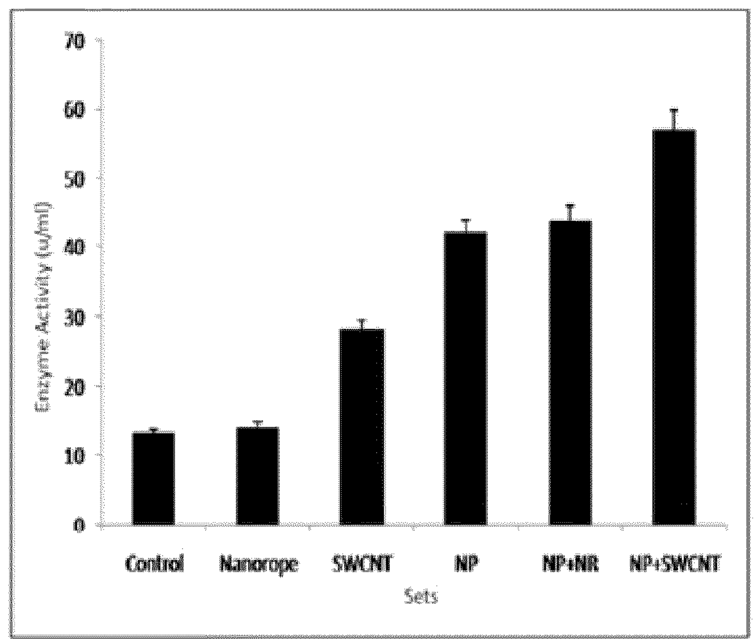

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Disclosed herein are compositions and methods related to the manufacture and use of stabilized psychrophilic or mesophilic enzymes. In some embodiments, the enzyme compositions and methods disclosed herein include (1) at least one psychrophilic enzyme, mesophilic enzyme, or a combination thereof; and (2) a plurality of lipid-functionalized graphenes, lipid-functionalized fullerenes, or lipid-functionalized carbon nanotubes, wherein the psychrophilic or mesophilic enzymes are entrapped by the lipid-functionalized graphenes, lipid-functionalized fullerenes, or lipid-functionalized carbon nanotubes but not linked to lipid-functionalized graphenes, lipid-functionalized fullerenes, or lipid-functionalized carbon nanotubes. In some embodiments, at least one nanoparticle is entrapped with the enzyme in the lipid-functionalized graphenes, lipid-functionalized fullerenes, or lipid-functionalized carbon nanotubes. The enzymes are in contact with, but not linked to, the nanoparticle.

As used in this specification and the appended claims, the singular forms “a”, “an” and “the” include plural referents unless the content clearly dictates otherwise. For example, reference to “a cell” includes a combination of two or more cells, and the like.

As used herein, “about” will be understood by persons of ordinary skill in the art and will vary to some extent depending upon the context in which it is used. If there are uses of the term which are not clear to persons of ordinary skill in the art, given the context in which it is used, “about” will mean up to plus or minus 10% of the particular term.

As used here in “substrate” in the context of psychrophilic or mesophilic enzyme refers to a molecule or a group of molecules upon which an enzyme acts. Enzymes catalyze chemical reactions involving the substrate(s). The substrate binds with the psychrophilic or mesophilic enzyme active site, and an enzyme-substrate complex is formed. The substrate is transformed into one or more products, which may then be released from the active site.

As used herein the term “enhanced activity” or “increased activity” in the context of enzymes refer to an enhanced or increased number of moles of substrate converted to product per unit time as compared to a suitable control enzyme. In some embodiments, enhanced activity of an enzyme may be exhibited under “optimal” or “standard conditions” for a particular type of enzyme (e.g., standard pH, standard temperature, standard substrate, etc.) as compared to a control enzyme under the same standard conditions. Additionally or alternatively, in some embodiments, enhanced activity may be exhibited under non-standard conditions for a particular type of enzyme (e.g., at a higher or lower temperature, higher or lower pH, non-optimal substrate, etc.) as compared to a control enzyme under the same conditions, or as compared to a control enzyme under standard conditions. By way of example, but not by way of limitation, disclosed herein are psychrophilic enzymes in contact with, but not linked, to at least one nanoparticle, wherein both enzyme and nanoparticle are entrapped by, but not linked to, lipid-functionalized graphenes, lipid-functionalized fullerenes, or lipid-functionalized carbon nanotubes, wherein the psychrophilic enzyme has enhanced activity as compared to a control psychrophilic enzyme (e.g., the same type of psychrophilic enzyme not in contact with at least one nanoparticle and not entrapped by carbon nanotubes, wherein the activity of the control enzyme is evaluated under the same conditions of temperature, buffer, pH, substrate, etc. as the psychrophilic enzyme in contact with the nanoparticles and entrapped by carbon nanotubes).

As used herein “enhanced half life” or “increased half life” in the context of psychrophilic or mesophilic enzyme refers to enhancement or increase in the amount of time the psychrophilic or mesophilic enzyme can retain 50% of its activity as compared a control enzyme.

As used herein “enhanced psychrophilic stability” or “increased psychrophilic stability” in the context of enzymes refers to an enhancement or increase in structural and/or functional integrity, and/or enzyme activity at a low temperature or a low temperature range outside the “normal” or “standard” temperature or temperature range for a given enzyme, as compared to a suitable control enzyme. By way of example, but not by way of limitation, in some embodiments of the compositions and methods disclosed herein, psychrophilic enzymes, which are in contact with, but not linked to, at least one nanoparticle, wherein both the enzyme and nanoparticle are entrapped by, but not linked to, the lipid-functionalized graphenes, lipid-functionalized fullerenes, or lipid-functionalized carbon nanotubes, exhibit higher stability and/or activity at about 2° C.-15° C., or at about 2° C., 3° C., 4° C., 5° C., 6° C., 7° C., 8° C., 9° C., 10° C., 11° C., 12° C. or 13° C., 14° C. or 15° C. as compared to a control psychrophilic enzyme (e.g., a psychrophilic enzyme not in contact with at least one nanoparticle and not entrapped by lipid-functionalized graphenes, lipid-functionalized fullerenes, or lipid-functionalized carbon nanotubes).

As used herein "enhanced thermal stability" or "increased thermal stability" or "enhanced temperature tolerance," in the context of enzymes refers to an enhancement or increase in structural and/or functional integrity, and/or enzyme activity at a high temperature or a high temperature range outside the "normal" or "standard" temperature or temperature range for a given enzyme, as compared to a suitable control enzyme. By way of example, but not by way of limitation, in some embodiments of the compositions and methods disclosed herein, psychrophilic enzymes in contact with, but not linked, to at least one nanoparticle, wherein both enzyme and nanoparticle are entrapped by, but not linked to, the lipid-functionalized graphenes, lipid-functionalized fullerenes, or lipid-functionalized carbon nanotubes exhibit higher stability and/or activity at about 35° C. to 80° C., or at about 35° C., 37° C., 40° C., 42° C., 45° C., 50° C., 55° C., 60° C., 65° C., 70° C., 75° C., or 80° C. as compared to a control psychrophilic enzyme (for example, a psychrophilic enzyme not in contact with at least one nanoparticle and not entrapped by lipid-functionalized graphenes, lipid-functionalized fullerenes, or lipid-functionalized carbon nanotubes).

As used herein, the terms "treated enzyme," "entrapped enzyme," "treated enzyme composition" and "enzyme composition" refer to compositions of the present technology including an enzyme entrapped by, but not linked to, lipid-functionalized graphenes, lipid-functionalized fullerenes, or lipid-functionalized carbon-nanotubes. In some embodiments, the terms treated enzyme, entrapped enzyme, and enzyme composition refers to compositions of the present technology including an enzyme in contact with, but not linked to, at least one nanoparticle, wherein both the enzyme and nanoparticle are entrapped, but not linked to, lipid-functionalized graphenes, lipid-functionalized fullerenes, or lipid-functionalized carbon-nanotubes.

As used herein in, "control psychrophilic enzyme," "control mesophilic enzyme," or "control enzyme" will have a meaning known to those of skill in the art and which will necessarily depend on the aspect of e.g., enzyme activity or conditions to be evaluated. Typically, a control or control enzyme will be compared to a test enzyme (e.g., an enzyme that has been modified or treated in some way). The control and the test enzyme will typically be the same type of enzyme and will be derived from the same source. The control enzyme will not undergo the "modification" or "treatment" (e.g., will not be contacted with nanoparticles, or will not be in a compositions comprising nanoparticles, or will not be in compositions entrapped by lipid-functionalized graphenes, lipid-functionalized fullerenes, or lipid-functionalized carbon nanotubes), but will be evaluated for enzymatic activity, pH tolerance, temperature tolerance, half-life, etc. under the same conditions as the "modified" or "treated" enzyme. Thus, the effects of the "modification" or "treatment" may be determined. In some embodiments, a "modification" or "treatment" includes entrapping an enzyme with lipid-functionalized graphenes, lipid-functionalized fullerenes, or lipid-functionalized carbon nanotubes, wherein the enzyme is not linked to the lipid-functionalized graphenes, lipid-functionalized fullerenes, or lipid-functionalized carbon nanotubes.

In some embodiments, the entrapped enzyme is in contact with, but not linked to, at least one nanoparticle.

As used herein, the phrase "but not linked to" refers to interactions between molecules that would not lead to the immobilization of one linking partner with the other linking partner, and/or would not create a permanent attachment of one linking partner with the other linking partner, and/or would not bind one linking partner with the other linking partner. By way of example, but not by way of limitation, "an enzyme entrapped by lipid-functionalized carbon nanotubes but not linked to the lipid-functionalized carbon nanotubes" refers to a lack of or absence of intermolecular bonds that lead to immobilization of the enzyme on the lipid-functionalized carbon nanotubes, creates a permanent attachment of enzyme to the lipid-functionalized carbon nanotubes, or binds the enzyme to the lipid-functionalized carbon nanotubes. Additionally, with reference to "an enzyme being in contact with a nanoparticle but not linked to a nanoparticle," "but not linked to" refers to a lack of or absence of intermolecular bonds that lead to the immobilization of the nanoparticle on the enzyme or creates a permanent attachment of the nanoparticle to the enzyme.

As used herein, the term "nanoparticle" refers to any particle in which the largest dimension is in the nanometer range, and/or wherein the particles have an average size in the nanometer range. For example, in some embodiments, the nanoparticle has a largest dimension of, or includes a composition comprising a plurality of nanoparticles has an average dimension that is, less than 1000 nm, for example, about 999 nm, about 900 nm, about 800 nm, about 700 nm, about 600 nm, about 500 nm, about 400 nm, about 350 nm, about 300 nm, about 200 nm, about 100 nm, or ranges between any two of these values. Additionally or alternatively, in some embodiments, the largest dimension of the nanoparticle, or the average size of a plurality of nanoparticles is, for example, about 100 nm, about 90 nm, about 80 nm, about 70 nm, about 60 nm, about 50 nm, about 25 nm, about 20 nm, about 10 nm, about 5 nm, about 3 nm, about 2 nm, about 1 nm or less, or ranges between any two of these values.

As used herein, the term "protease" (also termed peptidase or proteinase) refers to an enzyme that conducts proteolysis, that is, begins protein catabolism by hydrolysis of the peptide bonds that link amino acids together in the polypeptide chain forming the protein.

As used herein, "psychrophilic enzymes" refer to those enzymes which have optimal function or activity at about 0° C. to about 30° C. In some embodiments, the psychrophilic enzymes have optimal function or activity at temperature below about 10° C.

As used herein, "mesophilic enzymes" refer to those enzymes which have optimal function or activity at about 20° C. to about 45° C.

I. Enzyme Compositions

Disclosed herein are methods and compositions comprising enzymes entrapped by, but not linked to, lipid-functionalized graphenes, lipid-functionalized fullerenes, or lipid-functionalized carbon nanotubes. In some embodiments, the enzymes of the present technology comprise at least one psychrophilic enzyme, mesophilic enzyme, or combinations thereof. In some embodiments, at least one nanoparticle is entrapped with the enzyme, but not linked to the enzyme, in the lipid-functionalized graphenes, lipid-functionalized fullerenes, or lipid-functionalized carbon nanotubes. In some embodiments, the enzymes in the compositions may exhibit one or more characteristics of enhanced activity, enhanced temperature tolerance, and enhanced half-life as compared to a suitable control enzyme.

A. Psychrophilic Enzymes

The present technology is not limited by the type of psychrophilic enzyme, or the source of the enzyme. In some embodiments, psychrophilic enzymes may be isolated from natural sources (e.g., from psychrophilic prokaryotic or eukaryotic organisms such as bacteria or molds) or may be prepared recombinantly. In some embodiments, the psychrophilic enzymes may be "wild-type" or may be mutant, and may include one or more amino acid substitutions, additions or deletions as compared to the wild-type enzyme.

Non-limiting examples of psychrophilic enzymes which may be used in the compositions and methods disclosed herein include pectinase, laccase, xylanase, cellulase, and combinations thereof.

B. Mesophilic or Thermophilic Enzymes

Proteases disclosed herein may be mesophilic or thermophilic, and may be isolated from natural sources (e.g., from prokaryotic or eukaryotic organisms such as bacteria, yeast, molds, etc.) or may be prepared recombinantly. In some embodiments, the protease enzyme may be "wild-type" or may be mutant, and may include one or more amino acid substitutions, additions or deletions as compared to the wild-type enzyme.

C. Carbon Nanotubes and Other Carbon Structures

Nanotube and carbon structure based trapping methods of the present technology have a number of advantages over conventional enzyme immobilization methods. By way of example, but not by way of limitation, enzymes of the present technology are suspended in a colloid-like state and the effective surface active area is high. Additionally, nanotube based trapping methods disclosed herein allow for versatile (cross-enzyme) reusability, which conventional immobilization technique do not provide. Easy harvesting of the enzyme after its use makes the methods and compositions disclosed herein economic for the bio-processing activity of choice.

In some embodiments, the luciferase composition includes at least one luciferase is entrapped by, but not linked to, lipid-functionalized graphene or lipid-functionalized fullerene. Graphene and fullerene are carbon allotropes. Allotropy is the property of some chemical elements to exist in two or more different forms. Graphene, which can be stacked, comprises carbon atoms arranged in a regular hexagonal pattern. Fullerenes are any molecule composed entirely of carbon in the form of a hollow sphere or tube. Example of fullerenes include, but are not limited to, buckyballs (spherical fullerenes) and carbon nanotubes (cylindrical fullerenes).

In some embodiments of the present technology, the luciferase is entrapped by, but not linked to, lipid-functionalized carbon nanotubes. Examples of carbon nanotubes include, but are not limited to, single-wall carbon nanotubes (SWCNT), double-walled carbon nanotubes, or multi-walled carbon nanotubes. In some embodiments, the carbon nanotubes are solid state functionalized with lipids.

Lipids used to functionalize the graphenes, fullerenes, and carbon nanotubes include, but are not limited to, phospholipids, sphingolipids, phosphosphingolipids, and steroids. Typically, there are two fatty acid moieties present on the lipids used in the present technology: a long chain and a short chain.

In some embodiments, the chain length of the short chain lipid is between 2 carbons ("C") to 10 carbons ("C") long. In some embodiments the short chain is between 2C and 8C long. In some embodiments, the short chain is 2C, 3C, 4C, 5C, 6C, 7C, 8C, 9C or 10C long. In some embodiments, the long chain lipid length is 14-22C long. In some embodiments, the long chain is 14C, 15C, 16C, 17C, 18C, 19C, 20C, 21C, or 22C long.

In some embodiments, at least one long chain lipids (for example 22C) will allow the carbon nanotubes to entrap a larger enzyme. For example, at least one longer chain length lipids result in a larger nano-cage. Conversely, for example, shorter chain length lipids (for example 14C) result in a tighter nano-cage, which can entrap smaller complexes, but cannot entrap large complexes.

In some embodiments, the ratio of lipid to carbon nanotubes (wt/wt) is about 6:1, or about 5:1, or about 4:1, or about 3:1, or about 2:1.

In some embodiments, the lipid-functionalized carbon nanotubes have polar heads on one end of the tubes. In another embodiment, the lipid-functionalized carbon nanotubes have polar heads on both ends of the tubes.

Methods of functionalizing nanotubes are well known in the art. See e.g., Bhattacharyya et al., Nanotechnology, 23 (2012); 385304 (8 pp).

D. Nanoparticles

The nanoparticles provided in several illustrative embodiments described herein refer to any particle in which the largest dimension is in the nanometer range, and/or in the instance wherein the composition contains a plurality of nanoparticles, the dimension described herein can refer to an average of the individual dimensions of the plurality of the nanoparticles. For example, in some embodiments, the nanoparticle has a largest dimension that is less than 1000 nm, for example, about 999 nm, about 900 nm, about 800 nm, about 700 nm, about 600 nm, about 500 nm, about 400 nm, about 350 nm, about 300 nm, about 200 nm, about 100 nm, or ranges between any two of these values. Additionally or alternatively, in some embodiments, the largest dimension of the nanoparticle is, for example, about 100 nm, for example, about 90 nm, about 80 nm, about 70 nm, about 60 nm, about 50 nm, about 25 nm, about 20 nm, about 10 nm, about 5 nm, about 3 nm, about 2 nm, about 1 nm or less, or ranges between any two of these values.

As noted above, the dimension can refer to, for example, the largest dimension of the particle. Additionally or alternatively, the dimension can refer to the smallest dimension of the particle. The particle can have any shape. For example, the nanoparticles in some embodiments can refer to particles that are at least substantially spherical. Additionally or alternatively, nanoparticles can have a shape that is an ellipsoid, cube, cylindrical, or an irregular shape. Depending on the shape, the dimension described herein can refer to any of diameter, radius, width, length, height, diagonal, and the like. Also, in the instance wherein the composition contains a plurality of nanoparticles, the dimension described herein can refer to an average of the individual dimensions of the plurality of the nanoparticles. For example, in some embodiments, the average of the individual dimensions of the plurality of nanoparticles is about 1000 nm, about 999 nm, about 900 nm, about 800 nm, about 700 nm, about 600 nm, about 500 nm, about 400 nm, about 300 nm, about 200 nm, about 100 nm, or ranges between any two of these values. Additionally or alternatively, in some embodiments, the average of the individual dimensions of the plurality of nanoparticles is, for example, about 100 nm, about 90 nm, about 80 nm, about 70 nm, about 60 nm, about 50 nm, about 25 nm, about 20 nm, about 10 nm, about 5 nm, about 3 nm, about 2 nm, about 1 nm, or ranges between any two of these values.

In some embodiments, the nanoparticle has a shape that is at substantially spherical and a diameter of about 2 nm to about 500 nm, about 10 nm to about 500 nm, about 25 nm to about 500 nm, about 50 nm to about 400 nm, about 100 nm to about 400 nm, about 80 nm to about 100 nm.

In some embodiments, the entrapped enzyme composition contains nanoparticles. The nanoparticles are in contact with the enzyme, but the nanoparticles are not linked to the enzyme. Examples of nanoparticles include, but are not limited to, cuprous oxide, hydroxyapatite (HAp), magnesium chloride, manganese chloride, calcium chloride, zinc, magnesium, manganese, or a combination thereof.

II. Characteristics of the Enzyme Compositions

The entrapment of the psychrophilic enzymes or mesophilic enzymes by the methods disclosed herein results in enhanced enzymatic activity. In some embodiments, the entrapment of an enzyme (e.g., a psychrophilic enzyme or a mesophilic enzyme) results in one or more of enhanced enzymatic activity, enhanced pH tolerance, enhanced temperature tolerance, increased half-life, and/or the ability to withstand multiple freeze-thaw cycles and maintain a given level activity. In some embodiments, at least one nanoparticle is also entrapped with the enzyme in the lipid-functionalized carbon nanotubes, but the nanoparticles are not linked to the enzyme or lipid-functionalized carbon nanotubes.

1. Enhanced Thermophilic or Psychrophilic Stability

In some embodiments, enhance enzymatic activity is measured by thermophilic or psychrophilic stability. Psychrophilic enzymes are adapted to have high activity at low temperatures of about 0° C. to about 30° C. Additionally, psychrophilic enzymes usually possess a higher specificity than mesophilic counterparts. However, psychrophilic enzymes denature and lose their enzymatic activity at higher temperatures. The entrapped psychrophilic enzymes of the present technology have increased thermophilic stability and have higher enzymatic activity at higher temperatures compared to control psychrophilic enzymes.

Mesophilic enzymes also denature at high temperatures (for example, above about 60° C.), which leads to decreased mesophilic enzyme activity. The entrapped mesophilic enzymes of the present technology have increased thermophilic stability and have higher enzymatic activity at higher temperatures as compared to control mesophilic enzymes.

In some embodiments, the enhanced thermal stability or increased thermal stability of entrapped psychrophilic or mesophilic enzymes refers to enzyme activity at a temperature range from about 35° C. to about 80° C., from about 45° C. to about 70° C., or from about 55° C. to about 60° C. In some embodiments, the reference temperature in the context of thermal stability of entrapped psychrophilic or mesophilic enzymes is about 35° C., 37° C., 40° C., 42° C., 45° C., 50° C., 55° C., 60° C., 65° C., 70° C., 75° C., or 80° C., or ranges between any two of these values.

The present technology also enhances psychrophilic stability of psychrophilic and mesophilic enzymes. While psychrophilic enzymes are enzymatically active at lower temperatures, for example, below about 10° C., the entrapment of psychrophilic enzymes in lipid-functionalized carbon nanotubes with nanoparticles enhances the enzymatic activity of psychrophilic enzymes as compared to control psychrophilic enzymes.

Typically, mesophilic enzymes have an optimal enzymatic activity temperature of about 25° C. to about 45° C. As noted above, many mesophilic enzymes denature at high temperatures (for example, above about 60° C.), which leads to decreased mesophilic enzyme activity. Mesophilic enzymes also lose enzymatic activity when the temperature gets too low, for example, below about 25° C. The entrapment of mesophilic enzymes in lipid-functionalized carbon nanotubes with nanoparticles enhances the psychrophilic stability of mesophilic enzymes as compared to control mesophilic enzymes.

In some embodiments, the enhanced psychrophilic stability of psychrophilic or mesophilic enzyme refers to enzyme activity at a temperature of about 4° C. to about 30° C., or from about 8° C. to about 20° C., from about 12° C. to about 16° C. In some embodiments, the reference temperature in the context of psychrophilic stability of entrapped psychrophilic or mesophilic enzymes is about 4° C., 8° C., 12° C., 16° C., 20° C., 24° C., 28° C., or 30° C., or ranges between any two of these values.

2. Enhanced Enzyme Activity and Half-Life

Additionally or alternatively, in some embodiments, the enhanced activity or increased activity of a psychrophilic or mesophilic enzyme is determined by an increase in the maximum reaction velocity ($V_{max}$), an increase in turnover number, i.e., the number of substrate molecule each enzyme site converts to product per unit time, and/or an increase in substrate affinity for example, a decrease in Michaelis Constant ($K_m$), a decrease in the activation energy ($E_a$), or a combination thereof.

In some embodiments, the entrapped psychrophilic or mesophilic enzyme has a longer half-life and/or lower decay constant as compared to control psychrophilic or mesophilic enzyme. In some embodiments, the longer half-life and/or lower decay constant improves the entrapped enzyme's productivity, as the enzyme remains active for longer durations during a lengthy reaction process.

In some embodiments, the entrapped psychrophilic or mesophilic enzyme of the present technology retain enzymatic activity for a longer period of time as compared to the length of enzymatic activity of a control enzyme. In some embodiments, an entrapped enzyme composition retains enzymatic activity for about 1.5 hours to about 7 hours, or about 2 hours to about 6.5 hours, or about 3 hours to about 6 hours, or between about 3.5 hours to about 5.5 hours, or about 4 hours to about 5 hours. In some embodiments, the duration of enzymatic activity of entrapped enzymes is about 1.5 hours, 2 hours, 3 hours, 4 hours, 5 hours, 6 hours, or 7 hours, 8 hours, 9 hours, 10 hours, 11 hours, 12 hours or ranges between any two of these values. In some embodiments, the duration of enzymatic activity of entrapped enzymes is about 12 hours, 1 day, 2 days, 3 days, 4 days, 5 days, 6 days, 7 days, or ranges between any two of these values.

In some embodiments, the extended duration of enzymatic activity of entrapped enzymes as compared to control enzymes is observed at a temperature of about 4° C. to about 30° C., or from about 8° C. to about 20° C., from about 12° C. to about 16° C. In some embodiments, the temperature in the context of extended psychrophilic stability is about 4° C., 8° C., 12° C., 16° C., 20° C., 24° C., 28° C., or 30° C., or ranges between any two of these values.

In some embodiments, the extended duration of enzymatic activity of entrapped enzymes as compared to control enzymes is observed at a temperature of about 35° C. to about 80° C., from about 45° C. to about 70° C., or from about 55° C. to about 60° C. In some embodiments, the temperature in the context extended thermal stability is about 35° C., 37° C., 40° C., 42° C., 45° C., 50° C., 55° C., 60° C., 65° C., 70° C., 75° C., or 80° C., or ranges between any two of these values.

3. Stabilization of Enzymes after Freeze-Thaw Cycles

In some embodiments, the entrapped enzyme has enhanced enzyme activity after three or more freeze-thaw cycles as compared to control enzymes. In some embodiments, the entrapped enzymes maintain enzymatic activity up to 4 freeze-thaw cycles, or 5 freeze-thaw cycles, or 6 freeze-thaw cycles, or 7 freeze-thaw cycles, or 8 freeze-thaw cycles, or 9 freeze-thaw cycles. In some embodiments, the entrapped enzymes maintain enzymatic activity from about 9 freeze-thaw cycles to about 30 freeze-thaw cycles, or about 12 freeze-thaw cycles to about 27 freeze-thaw cycles, or about 15 freeze-thaw cycles to about 24 freeze-thaw cycles, or about 18 freeze-thaw cycles to about 21 freeze-thaw cycles.

III. Methods for Entrapping Enzymes and Nanoparticles

In some embodiments, the formation of an enhanced enzyme composition includes combining lipid-functionalized carbon nanotubes, fullerenes and/or graphenes, e.g., lipid-functionalized SWCNT, and at least one psychrophilic enzyme, mesophilic enzyme, or a combination thereof, and sonicating the combination. The lipid-functionalized carbon nanotubes (or graphenes or fullerenes) will self-assemble into a "nano-cage" after sonication. In some embodiments, the formation of the nano-cage entraps the enzymes. In some embodiments, at least one nanoparticle is also entrapped with the enzymes in the nano-cage. In some embodiments, the nanoparticle is entrapped with the enzymes in the nano-cage, but is not linked to the enzyme or the nano-cage.

In some embodiments, the ratio of lipid-functionalized graphenes, lipid-functionalized fullerenes, or lipid-functionalized carbon nanotubes to enzyme (wt/wt) is 6:1, or about 5:1, or about 4:1, or about 3:1, or about 2:1.

By way of example, but not by way of limitation, in some embodiments, the amounts of lipid-functionalized SWCNT (0.5 mg/ml), pectate lyase (0.18 mg/ml), laccase (0.25 mg/ml), cellulase (0.11 mg/ml), xylanase (0.2 mg/ml) and protease (0.22 mg/ml) are $5\times10^{-3}$ mg, $18\times10^{-3}$ mg, $25\times10^{-3}$ mg, $11\times10^{-3}$ mg, $20\times10^{-3}$ mg and $22\times10^{-3}$ mg respectively. In some embodiments, the amount of SWCNT is between 0.1-1.0 mg/ml. In some embodiments, pectate lyase is between 0.1 to 0.25 mg/ml. In some embodiments, laccase is between about 0.15 to 0.50 mg/ml. In some embodiments, cellulase is between 0.005 to 0.4 mg/ml. In some embodiments, xylanase is between 0.1 mg/ml to 0.5 mg/ml. In some embodiments, protease is between 0.1 mg/ml to 0.5 mg/ml.

IV. Methods for Using the Enzyme Composition—General

In some embodiments, at least one entrapped enzyme is contacted with at least one substrate. In some embodiments the contacting is performed at a temperature of about 4° C. to about 30° C., or about 8° C. to about 26° C., or about 12° C. to about 22° C., or about 16° C. to about 18° C. In some embodiments, the contacting is performed at a temperature about 4° C., 8° C., 12° C., 16° C., 20° C., 24° C., 28° C., or 30° C., or ranges between any two of these values. In some embodiments, the contacting is performed at a temperature of about 0° C. to about 4° C.

In some embodiments the contacting is performed at a temperature of about 35° C. to about 80° C., or about 45° C. to about 70° C., or from about 55° C. to about 60° C. In some embodiments, the contacting is performed at a temperature about 35° C., 37° C., 40° C., 42° C., 45° C., 50° C., 55° C., 60° C., 65° C., 70° C., 75° C., or 80° C., or ranges between any two of these values.

In some embodiments, the contacting is performed for about 1.5 hours to about 7 hours, or about 2 hours to about 6.5 hours, or about 3 hours to about 6 hours, or about 3.5 hours to about 5.5 hours, or about 4 hours to about 5 hours. In some embodiments, the duration of contacting is about 1.5 hours, 2 hours, 3 hours, 4 hours, 5 hours, 6 hours, or 7 hours, or ranges between any two of these values. In some embodiments, the duration of enzymatic activity of entrapped enzymes is about 12 hours, 1 day, 2 days, 3 days, 4 days, 5 days, 6 days, 7 days, or ranges between any two of these values.

In some embodiments, the entrapped enzymes maintain high enzyme activity when used in multiple reactions as compared to a control enzyme. An example of the multiple reaction use of entrapped enzymes is as follows: 1) at least one entrapped enzyme is contacted with more than one substrate for the duration of a first reaction process; 2) after the completion of the first reaction process, the entrapped enzyme is collected; and 3) the collected entrapped enzymes are then used in a second reaction process. During the second reaction process, the entrapped enzyme maintains a high level of enzymatic activity, as measured by percent relative active. In some embodiments, entrapped enzymes are used in one reaction, or two reactions, or three reactions, or four reactions, or five reactions, or six reactions. In some embodiments, the reactions are run consecutively.

In some embodiments, the entrapped enzymes retain about 85% to about 99% of their enzymatic activity when re-used in a second reaction. In some embodiments, the entrapped enzymes retain about 80% to about 99%, or about 80% to about 95% of their enzymatic activity when re-used in a third reaction. In some embodiments, the entrapped enzymes retain between about 60% to about 99%, or about 60% to about 85% of their enzymatic activity when re-used in a fourth reaction. In some embodiments, the entrapped enzymes retain about 60% to about 99%, or about 60% to about 75% of their enzymatic activity when re-used in a fifth reaction.

V. Kits

In some embodiments, the entrapped enzyme compositions are presented in a kit. In some embodiments, the kit comprises a container with at least one entrapped enzyme composition, wherein the entrapped enzyme composition includes at least one enzyme entrapped in, but not linked to, lipid-functionalized graphenes, lipid-functionalized fullerenes, lipid-functionalized carbon nanotubes, or a combination thereof. In some embodiments, the entrapped enzyme composition includes nanoparticles. In some embodiments, the nanoparticles are in contact with the enzymes, but are not linked to the enzyme. In some embodiments, the nanoparticles are in contact with the nano-cage, but are not linked to the nano-cage. In some embodiments, the kit further includes instructions for applying the enzyme composition for the treatment of wide variety of organic and inorganic substrates.

In an alternative embodiment, the kit includes a first container having a plurality of lipid-functionalized graphenes, lipid-functionalized fullerenes, lipid-functionalized carbon nanotubes, or a combination thereof and a second container having at least one enzyme. In some embodiments, the kit includes a third container of at least one nanoparticle. In some embodiments, the kit also includes instructions to make an entrapped enzyme composition.

In some embodiments, the enzymes are one or more of psychrophilic enzymes, mesophilic enzymes, or a combination thereof. Psychrophilic enzymes include, but are not limited to, pectinase, laccase, cellulase, and xylanase. Mesophilic enzymes include, but are not limited to, protease.

In some embodiments, carbon nanotubes include, but are not limited to, single-wall carbon nanotubes, double-walled carbon nanotubes, or multi-walled carbon nanotubes. In some embodiments, the carbon nanotubes are solid state functionalized with lipids.

Nanoparticles include, but are not limited to, cuprous oxide, hydroxyapatite (HAp), magnesium chloride, manganese chloride, calcium chloride, or a combination thereof.

VI. Illustrative Uses of the Enzyme Compositions Disclosed Herein

A. Illustrative Uses of Microbial Heat-Stable Enzymes—General

Running biotechnological processes at elevated temperature has many advantages. In some processes, the increase of temperature can have a significant influence on the bioavailability and solubility of organic compounds. For example, the elevation of temperature may be accompanied by a decrease in viscosity and an increase in the diffusion coefficient of organic compounds. Accordingly, thermostable enzyme compositions of the present disclosure are useful in such processes. By way of example but not by way of limitation, chemical scouring is one process in which thermostable enzyme compositions of the present technology would be of value. Numerous additional illustrative uses of thermostable enzymes are discussed below.

Violent, hazardous chemicals like soda-ash, oxalic acid, caustic soda, used in chemical scouring process, cause environmental pollution and weaken the fibre strength of the product undergoing the scouring process (for example, wool).

On an industrial scale, chemical scouring is common. The process improves water absorbency and whiteness of textiles by removing non-cellulosic substances from many natural fibers.

Despite the interest in using enzymes, for example laccase, for bio-scouring processes, enzymes currently in use suffer from a lack of scouring efficiency. Lack of scouring efficiency can arise from thermal instability and low activity of the enzyme. Thermal instability results in reduction of activity over time due to thermally induced changes in enzyme conformations. Higher temperature accelerates reduction in activity. Low activity limits the rate at which scouring can occur. Scouring efficiency can be increased by using compositions of the present technology because the enzymes have increased thermostability and enzymatic activity, as described herein.

B. Illustrative Uses of Microbial Cold-Stable Enzymes—General

The high activity of psychrophilic enzymes at low and moderate temperatures offers potential economic benefits, for example, through substantial energy savings in large-scale processes that would not require the expensive heating of reactors. Psychrophilic enzymes can also be useful in domestic processes. For instance, washing clothes at low temperatures can protect the colours of fabrics (and reduce energy consumption). In the food industry, their properties allow the transformation or refinement of heat-sensitive products, as example, cold-active pectinases can help to reduce viscosity and clarify fruit juices at low temperatures. The heat-lability of these enzymes also ensures their fast, efficient, and selective inactivation in complex mixtures.

Psychrophilic microorganisms have also been proposed for the bioremediation of polluted soils and waste waters during the winter in temperate countries, when the degradative capacity of the endogenous micro-flora is impaired by low temperatures.

Cold-adapted enzymes are beneficial for their enhanced selectivity and high catalytic activity at low and moderate temperatures, in addition to their structural lability that can be exploited in multi-step processes requiring rapid and mild inactivation treatments. Furthermore, the inherent conformational plasticity of cold-adapted enzymes may be particularly suited to organic synthesis applications under the low water conditions used during the production of many fine chemicals and pharmaceutical intermediates.

C. General Uses of the Enzyme Compositions of the Present Technology

The high activity of the treated enzyme compositions of the present technology at low, moderate, and high temperatures offers potential economic benefits, for example, through substantial energy savings in large-scale processes that would not require the expensive heating of reactors. The treated enzyme compositions can also be useful in domestic processes. For instance, washing clothes at low temperatures can protect the colours of fabrics (and reduce energy consumption). In the food industry, their properties allow the transformation or refinement of heat-sensitive products, as example, cold-active pectinases can help to reduce viscosity and clarify fruit juices at low temperatures.

The treated enzyme compositions of the present technology may also be used for the bioremediation of polluted soils and waste waters during the winter in temperate countries, when the degradative capacity of the endogenous micro-flora is impaired by low temperatures.

The treated enzyme compositions of the present technology are beneficial for their enhanced selectivity and high catalytic activity at low and moderate temperatures, in addition to their structural lability that can be exploited in multi-step processes requiring rapid and mild inactivation treatments. Furthermore, the inherent conformational plasticity of cold-adapted enzymes may be particularly suited to organic synthesis applications under the low water conditions used during the production of many fine chemicals and pharmaceutical intermediates.

The enzyme composition of the present technology can be used for a variety of purposes. For example, the enzyme composition provides robust catalytic alternatives for the breakdown of lignocellulosic materials under industrial processing temperature. In some embodiments, the enzyme composition of the present technology can be used for bio-bleaching of fibers and cottons. The enzyme compositions can be used in the textile and paper industries in environmentally friendly methods. In some embodiments, the enzyme composition can be used for treatment of industrial wastewater containing phenolic, arylamine, diamine materials, and textile dye reagents. In some embodiments, the enzyme composition can be used for detoxification of industrial effluents. In some embodiments, the enzyme composition can be used for retting or bioscouring of natural bast fibers (for example, hemp and flax), and cotton fabric. In some embodiments, the enzyme composition can be used as an efficient tool for bioremediation.

For example, in some embodiments, the enzyme composition can be used to treat a substrate, where the substrate includes a phenolic hydroxyl group by contacting and/or incubating the substrate with a composition. In some embodiments, the substrate comprises an azo group. In some embodiments, the substrate comprises syringaldazine, congo red, cotton blue, bromophenol blue, malachite green. In some embodiments, the substrate comprises ortho and paradiphenols, aminophenols, polyphenols, polyamines, lignins and/or aryl diamines. In some embodiments, the substrate comprises a textile, wool, biocomposite, wastewater, paper, wood pulp, soil, animal feed, food, beverage, herbicide, pesticide, dye, pigment or combinations thereof. In some embodiments, the substrate comprises wood pulp comprising lignin.

In some embodiments, the substrate comprises dye or pigment, wherein the enzyme reacts with the dye or pigment and reduces the color of the substrate or decolorizes the substrate. In some embodiments, the substrate comprises a textile comprising a dye, wherein the enzyme reacts with the dye or pigment and reduces the color of the textile or decolorizes the textile. In some embodiments, the substrate comprises a beverage comprising phenolic compounds, wherein the enzyme reacts with the phenolic compound to reduce or remove browning or haze from the beverage. In some embodiments, the beverage is selected from fruit juice, beer, or wine.

In some embodiments, enzyme compositions disclosed herein comprising laccase may acts on phenolic substrates by catalyzing the oxidation of their phenolic hydroxyl groups to phenoxy radicals while dioxygen ($O_2$) is reduced to water. Enzymatic oxidation techniques have potential within a great variety of industrial fields including the pulp and paper, textile and food industries.

In some embodiments, enzyme compositions disclosed herein comprising pectinase enzyme have a wide variety of uses. By way of example, but not by way of limitation, such enzyme compositions are useful in food processing, and for catalyzing chemical reactions that lead to quality improvement of food products. Enzyme compositions disclosed herein comprising pectinase have several uses in the paper and pulp industry, textile, fruit juice industries, etc.

In some embodiments, enzyme compositions disclosed herein comprising cellulases are useful in various industries including pulp and paper, textile, laundry, biofuel production, food and feed industry, brewing, and agriculture. Due to the complexity of enzyme system and immense industrial potential, cellulases have been a potential candidate for research by both the academic and industrial research groups.

In some embodiments, enzyme compositions disclosed herein comprising xylanase are useful in biotechnology; exemplary uses include bio bleaching of wood pulp, treating animal feed to increase digestibility, processing food to increase clarification and converting lignocelluloses substances to feedstock and fuels.

In some embodiments, enzyme compositions disclosed herein comprising proteases are useful hydrolytic composition, and are useful in detergents, foods pharmaceuticals, leathers, diagnostics, waste management and silver recovery. In some embodiments, the protease is a bacterial protease.

Exemplary, non-limiting uses of the enzyme compositions of the present technology are provided below.

D. Detergents and Cleaning Products

In some embodiments, the enzyme compositions disclosed herein may be used as detergents. In some embodiments, the detergents efficiently hydrolyze soils and stains at low temperatures, thereby reducing energy consumption, which results in decreased associated costs and environmental impacts. Additionally, garment alterations that take place during warm- and hot-water wash cycles, such as fabric degradation, shrinkage and dye bleeding, will be reduced. Given the trend of decreasing wash temperatures, particularly in Europe and Japan, the enzyme compositions of the present technology are capable of working efficiently under low to medium-temperature conditions in detergents.

For example, in some embodiments, the enzyme composition comprises a cellulase, and the enzyme composition is used to produce a cellulase-based detergent. Cellulase-based detergents comprising psychrophilic cellulase enzyme composition of the present technology have superior cleaning action without damaging fibers, improve color brightness and dirt removal, remove rough protuberances in cotton fabrics, and provide antiredeposition of ink particles.

In some embodiments, the protease compositions of the present technology are useful in detergents for their ability to aid in the removal of proteinaceous stains and to deliver unique benefits that cannot otherwise be obtained with conventional detergent technologies. For example, in some embodiments, the detergents comprising a proteases composition of the present disclosure have improved performance/cost ratios, increased activity and improved compatibility with other detergent ingredients.

E. Paper Products and Paper Making

In some embodiments, the enzyme compositions of the present technology are used in paper making. Pulp and paper mills are beginning to use enzymes to solve problems in their manufacturing processes. Papermaking is essentially a continuous filtration process in which a dilute suspension of fibers, fiber fragments (fines), and inorganic filler particles, such as clay. Prominent among these polysaccharides are pectins, or polygalacturonic acids. The ability of polygalacturonic acids to complex cationic polymers (cationic demand) depends strongly on their degree of polymerization, monomers, dimers, and trimers of galacturonic acid do not cause measurable cationic demand, but hexamers and long chains have high cationic demand. Pectinase compositions of the present disclosure, for example, may be used to depolymerize polymers of galacturonic acids, and subsequently lower the cationic demand of pectin solutions and the filtrate from peroxide bleaching.

In some embodiments, the enzyme compositions of the present technology are used in the production of Japanese paper. For example, alkaline pectinase compositions of the present technology produced by *Bacillus* sp. and *Erwinia carotovora*, due to its strong macerating activity, is useful for retting of Mitsumata bast. These retted basts are used for the preparation of Japanese paper. In some embodiments, the strength of the pulp from bacterial retting using the compositions of the present disclosure, is as high as that obtained by the conventional soda-ash cooking method. The paper sheets prepared from this pulp are very uniform and soft to touch.

The industrial preparation of paper includes separation and degradation of lignin in wood pulp. Environmental concerns are focused on replacing conventional and polluting chlorine-based delignification/bleaching procedures. Accordingly, the psychrophilic ligninolytic (lignin-degrading) enzymes (laccase) compositions of the present disclosure may be used for the (pre)treatment of lignocelluloses raw material such as wood chips in pulping; this is referred to as bio pulping. Bio-pulping using the enzyme compositions of the present technology is applicable to both mechanical and chemical pulps; advantages include reduced refining energy or increased mill throughput in mechanical pulping, and enhanced paper strength properties, alleviated pitch problems, improved yield, and reduced environmental impact in mechanical and chemical pulping and papermaking. In some embodiments, the enzyme compositions of the present technology can be applied in the industrial preparation of paper. For example, psychrophilic laccase compositions as disclosed herein have may be used to activate the fibreboard lignin during manufacturing of the composites, thus, resulting in boards with good mechanical properties without toxic synthetic adhesives. In some embodiments, laccase compositions of the present technology may be used to graft various phenolics acid derivatives onto Kraft pulp fibers. Additionally, psychrophilic xylanase enzyme compositions of the present disclosure may be useful in the removal of residual lignin from Kraft pulp. Residual lignin from the Kraft process is physically and chemically restricted by hemicelluloses. Lignin can link with hemicelluloses, and there has been isolation of lignin carbohydrate complexes from the Kraft pulp. Hemicellulose is a substrate of xylanase.

In some embodiments, the enzyme compositions of the present technology can be applied in the production of pulp and paper. For example, cellulase compositions as disclosed herein can be used as a co-additive in pulp bleaching; biomechanical pulping; improved draining; enzymatic drinking; reduced energy requirement; reduced chlorine requirement; improved fiber brightness, strength properties, and pulp freeness and cleanliness; improved drainage in paper mills; production of biodegradable cardboard, paper towels, and sanitary paper.

In some embodiments, the enzyme compositions of the present technology can be applied to the reduce paper industry environmental pollution. For example, chlorinated phenolic compounds as well as polychlorinated biphenyls, produced during conventional pulp bleaching, are toxic and highly resistant to biodegradation and form one of the major sources of environmental pollution. Xylanase compositions of the present disclosure can be used in a chlorine-free wood pulp bleaching process.

F. Wastewater and Waste Treatment

Paper and pulp mills, molasses based-alcohol distilleries, tanneries, dye-making units and textiles are some of the major industries that produce and discharge highly colored effluents. Each of these industrial effluents creates some specific problem besides producing aesthetically unacceptable intense coloring of soil and water bodies. They block the passage of light to the lower depths of the aquatic system resulting in cessation of photosynthesis, leading to anaerobic conditions, which in turn result in the death of aquatic life causing foul smelling toxic waters.

The pollution problems due to the industrial effluents have increased in the recent years. The dyeing processes have, in general, a low yield and the percentage of the lost dye in the effluents can reach up to 50%. For example, textile dye effluents are complex, containing a wide variety of dyes, natural impurities extracted from the fibers and other products such as dispersants, leveling agents, acids, alkalis, salts and sometimes heavy metals. In general, the effluent is highly colored with high biological oxygen demand (BOD), suspended solids (SS), toxicity, and chemical oxygen demand (COD), it has a high conductivity and is alkaline in nature. The degradation products of the dyes are often carcinogenic. To meet stringent environmental regulations, the wastewaters have to be treated before their discharge to the environment. Most currently existing processes to treat dye wastewater are ineffective and not economical. Therefore, the development of processes based on the composition comprising laccase as described above, seems an attractive solution due to their potential in degrading dyes of diverse chemical structure, including synthetic dyes currently employed in the industry. The enzyme compositions of the present technology, for example comprising laccase enzyme, are able to detoxify wastewater containing chlorophenols by catalyzing their polymerization via radical coupling. The coupling products can be removed from the wastewater by precipitation. Chlorophenols can also cross-couple and precipitate with other phenols present in wastewater, which may enhance their removal efficiency.

In some embodiments, the enzyme compositions of the present technology are used in the treatment of pectic wastewater. The wastewater from the citrus-processing industry contains pectinaceous materials that are barely decomposed by microbes during the activated-sludge treatment. Accordingly, pectinase-containing enzyme compositions of the present technology are useful to treat pectic wastewater.

G. Food, Beverage, Feed Industry, Pharmaceutical and Cosmetic

In some embodiments, the enzyme compositions disclosed herein are particularly attractive for the processing of foods due to their high catalytic activity at temperatures that minimize spoilage and alterations in taste and nutritional values. Their inherent low structural stability also facilitates inactivation once a desired product is attained.

The enzyme compositions of the present technology exhibit high catalytic activities at low and ambient temperatures and can also be exploited for the pharmaceutical industry. The increasing demand for enantiomerically-pure drugs and pharmaceutical intermediates has led to a rapid expansion of the use of biocatalysts in organic synthesis.

In the cosmetic industry, psychrophilic enzyme compositions of the present technology can enhance the yield of biotransformation involving volatile substrates, such as flavor and fragrance compounds subject to evaporation at high temperatures.

By way of example, but not by way of limitation, in some embodiments, the enzyme compositions of the present technology can be applied to processes that enhance or modify the color appearance of food, animal feed or beverages. The enzyme compositions of the present technology are useful in the elimination of undesirable phenolics, responsible for the browning, haze formation and turbidity development in clear fruit juice, beer and wine. In some embodiments, the enzyme compositions are used in different aspects of the food industry such as bioremediation, beverage processing, ascorbic acid determination, sugar beet pectin gelation, baking and as a biosensor.

In some embodiments, the enzyme compositions of the present technology are used in coffee and tea fermentation. For example, pectinases play an important role in coffee and tea fermentation. Fermentation of coffee using pectinolytic microorganisms is done to remove the mucilage coat from the coffee beans. Pectic enzymes are sometimes added to remove the pulpy layer of the bean, three fourths of which consists of pectin substances.

Fungal pectinases are also used in the manufacture of tea. Enzyme treatment accelerates tea fermentation, although the enzyme dose must be adjusted carefully to avoid damage to the tea leaf. The addition of pectinase also improves the foam-forming property of instant tea powders by destroying tea pectins.

In some embodiments, the enzyme compositions of the present technology can be applied in fermentation. For example, cellulase can be used for improving malting and mashing; improved pressing and color extraction of grapes; improved aroma of wines; improved primary fermentation and quality of beer; improved viscosity and filterability of worth; improved must clarification in wine production; improved filtration rate and wine stability.

In some embodiments, the enzyme compositions of the present technology can be applied in food production. For example, cellulase plays a role in the release of the antioxidants from fruit and vegetable pomace; improvement of yields in starch and protein extraction; improved maceration, pressing, and color extraction of fruits and vegetables; clarification of fruit juices; improved texture and quality of bakery products; improved viscosity fruit purees; improved texture, flavor, aroma, and volatile properties of fruits and vegetables; controlled bitterness of citrus fruits.

H. Biofuels

In some embodiments, the enzyme compositions of the present technology are useful to make biofuels, such as ethanol made from the fermentation of carbohydrates produced in plants. Biofuels made with the enzyme compositions of the present technology represent a renewable energy source that can provide a myriad of other benefits, including increased energy security, a reduction in greenhouse gas emissions, economic benefits for rural communities, and mitigating problems associated with disposal of agro-industrial residues. All fuel ethanol is currently produced by fermentation of starchy crop-based sugars, industrial enzyme companies are pursuing methods for inexpensive ethanol production from low-cost lignocellulosic biomass, including agricultural waste, forestry waste, energy crops, and municipal solid waste. By way of example, but not by way of limitation, compositions comprising cold-adapted glycosyl hydrolases such as cellulases, xylanase and glycosidase of the present technology may enable cost-effective lignocellulose biomass conversion, thus facilitating the development of an economically-viable and renewable source of fuel to meet the world's increasing energy demands.

I. Enzyme Nanobiotechnology

In some embodiments, the enzyme compositions of the present technology are useful for synthesizing nanostructured materials at low temperatures and mild conditions. This results in inexpensive, environmentally-friendly alternatives to traditional synthesis techniques.

J. Exemplary Applications Using Laccase

Laccases can act on a wide range of substrate. It has the ability to oxidise both phenolic and nonphenolic lignin related compounds as well as highly recalcitrant environmental pollutants, which makes them very useful for their application to several biotechnological processes. Such applications include the detoxification of industrial effluents, mostly from the paper and pulp, textile and petrochemical industries, use as a tool for medical diagnostics and as a bioremediation agent to clean up herbicides, pesticides and certain explosives in soil. Laccases are also used as cleaning agents for certain water purification systems, as catalysts for the manufacture of anti-cancer drugs and even as ingredients in cosmetics. In addition, their capacity to remove xenobiotic substances and produce polymeric products makes them a useful tool for bioremediation purposes.

1. Laccase in the Degradation of Lignocellulosic Materials

The enzyme compositions of the present technology comprising laccase are useful in degrading lignocellulosic materials. The enzyme compositions can be used, for example, to initiate a series of redox reactions, which degrade the lignin (or lignin-derived pollutants). The enzyme compositions can be used to oxidize aromatic compounds until the aromatic ring structure is cleaved, which can then be followed by additional degradation with other enzymes. The breakdown of lignocellulosic materials has wide variety of industrial applications.

Enzymatic hydrolysis of lignocellulosic materials is the first step for either digestion to biogas (methane) or fermentation to ethanol. Ethanol is an important renewable bio-fuel in terms of volume and market value. The demand for ethanol has a significant market, as ethanol is commonly used as a chemical feedstock or as an octane enhancer or petrol additive. Hence, the enzyme compositions of the present technology is useful in the production of ethanol from lignocellulosic materials.

Biogas is another energy source that is used as car fuel, or for production of heat or electricity. Pretreatment of lignocellulosic materials with the enzyme compositions of the present technology would degrade the lignocellulosic materials and help to produce ethanol and biogas.

Bioconversion of lignocellulosic breakdown wastes could make a significant contribution to the production of organic chemicals.

In some embodiments, the enzyme composition of the present technology can be used to produce vanillin. Vanillin is an exemplary bio-product of lignin breakdown. The largest use of vanillin is as a flavoring, usually in sweet foods. It is used in the flavor industry, as a very important key note for many different flavors, especially creamy profiles. The ice cream and chocolate industries together comprise 75% of the market for vanillin as a flavoring, with smaller amounts being used in confections and baked goods. Vanillin is also used in the fragrance industry, in perfumes to mask unpleasant odors or tastes in medicines, livestock fodder, and cleaning products. Vanillin has been used as a chemical intermediate in the production of pharmaceuticals and other fine chemicals.

2. Laccase in Organic Synthesis

In some embodiments, the enzyme composition of the present technology comprising laccase can be employed for several applications in organic synthesis, e.g., the oxidation of functional groups, the coupling of phenols and steroids.

In some embodiments, the enzyme composition of the present technology comprising laccase can be used to aerobically convert phenol to catechol. Catechol is the precursor to pesticides, flavors, and fragrances. Approximately 50% of synthetic catechol is consumed in the production of pesticides, the remainder being used as a precursor to fine chemicals such as perfumes and pharmaceuticals.

Catechol is a common building block in organic synthesis. Several industrially significant flavors and fragrances are prepared starting from catechol. Guaiacol is prepared by methylation of catechol and is then converted to vanillin. The related monoethyl ether of catechol, guethol, is converted to ethylvanillin, a component of chocolate confectioneries. 3-Trans-Isocamphylcyclohexanol, widely used as a replacement for sandalwood oil, is prepared from catechol via guaiacol and camphor. Piperonal, a flowery scent, is prepared from the methylene diether of catechol followed by condensation with glyoxal and decarboxylation.

The enzyme compositions of the present technology are useful to oxidize phenolic compounds (e.g., phenols, polyphenols, meta substituted phenols), diamines and a variety of other components utilizing molecular oxygen. In some embodiments, the enzyme compositions of the present technology are useful in the synthesis of quinones by oxidizing phenols and catechols. A large scale industrial application of quinones is for the production of hydrogen peroxide. 2-Alkylanthraquinones are hydrogenated to the corresponding hydroquinones (quinizarins), which then transfer $H_2$ to oxygen.

Derivatives of quinones are common constituents of biologically relevant molecules (e.g., Vitamin K1 is phylloquinone). Natural or synthetic quinones show a biological or pharmacological activity, and some of them show antitumoral activity and possess a number of biological properties, including some claims in herbal medicine. These applications include purgative (sennosides), antimicrobacterial (rhein- and saprorthoquinone), anti-tumor (emodin and jugone), inhibition of PGE2 biosynthesis (arnebinone and arnebifuranone) and anti-cardiovascular disease (tanshinone).

Many natural and artificial coloring substances (dyes and pigments) are quinone derivatives. They are second only to azo dyes in importance as dyestuffs, with particular emphasis on blue colors. Alizarin (2,3-dihydroxy-9,10-anthraquinone), extracted from the madder plant, was the first natural dye to be synthesized from coal tar.

3. Exemplary Use of Laccase in Textile Industries

The laccase enzyme compositions of the present technology, with enhanced activity at higher temperatures, are useful in wool dyeing, rove scouring, anti-shrink treatment of wool, and dye synthesis.

In textile processing, laccase enzyme compositions of the present technology can be used for improving the fabric whiteness in bleaching process, decolorization of dyed textile materials and colored effluent and scouring of fibers, wool dyeing, and wool anti-felting. Laccase enzyme compositions of the present technology can be used to color wool fabric that was previously padded with hydroquinone. Laccase enzyme compositions of the present technology can be used for wool dyeing. A dye bath can be prepared with a dye precursor (2,5-diaminobenzene-sulfonic acid), dye modifiers (catechol and resorcinol) and laccase, without any dyeing auxiliaries.

Laccase enzyme compositions of the present technology is useful for reducing felting shrinkage of wool fabric. Increasing concentration of laccase can lead to a decrease in fabric shrinkage.

Laccase enzyme compositions of the present technology can be used for roving treatment to improve yarn regularity. The advantage of the use of laccase in rove scouring is that the process is performed under mild reaction conditions resulting, thus, in an ecologically friendly process.

Laccase enzyme compositions of the present technology can be used to form red azo dyes by the oxidative coupling of 3-methyl-2-benzothiazolinone hydrazone (MBTH) and phenols. Oxidation of ferulic acid by laccase in a biphasic hydro-organic medium leads to the production of stable yellow coloured products.

a. Denim Finishing

In the textile finishing industry, enzymatic degradation of indigo could have potential both in stone-wash process and for the treatment of dyeing effluents. Several steps are involved in the manufacture of denim garments between dyeing and the final stone-washing where excessive amounts of indigo are removed from the fabrics and discharged with the wastewater. The fabrics are partially bleached by a treatment with sodium hypochlorite, followed by neutralization and a rinsing step all causing substantial environmental pollution. The enzyme compositions of the present technology, for example having the laccase enzyme, are useful in denim finishing.

b. Cotton Bio-Bleaching

The purpose of cotton bleaching is to decolorize natural pigments and to confer a pure white appearance to the fibers. Mainly flavonoids are responsible for the color of cotton. The most common industrial bleaching agent is hydrogen peroxide. However, radical reactions of bleaching agents with the fiber can lead to a decrease in the degree of polymerization and, thus, to severe damage. Furthermore, a huge amount of water is needed to remove hydrogen peroxide from fabrics, which can cause problems in dyeing. Therefore, replacement of hydrogen peroxide by an enzymatic bleaching system would not only lead to better product quality due to less fiber damage but also to substantial savings on washing water needed for the removal of hydrogen peroxide.

In some embodiments, the enzyme compositions of the present technology are used to enhance the bleaching effect on cotton fabrics. For example, it has been reported that the bleaching effect is enhanced on cotton fabrics by using laccases in low concentrations. Also, enzyme composition of the present technology comprising laccase can improve the whiteness of cotton due to oxidation of flavonoids. For example, studies have shown that a laccase from a newly isolated strain of *T. hirsuta* was responsible for whiteness improvement of cotton most likely due to oxidation of flavonoids. In addition, the short time of the enzymatic pretreatment sufficient to enhance fabric whiteness makes this bio-process suitable for continuous operations.

K. Applications Using Cellulase

1. Cellulase in Agriculture

In some embodiments, the enzyme compositions of the present technology can be applied in agriculture. Plant pathogen and disease control; generation of plant and fungal protoplasts; enhanced seed germination and improved root system; enhanced plant growth and flowering; improved soil quality; reduced dependence on mineral fertilizers.

2. Cellulase in Bioconversion

In some embodiments, the enzyme compositions of the present technology can be applied in bioconversion. For example, conversion of cellulosic materials to ethanol, other solvents, organic acids and single cell protein, and lipids; production of energy-rich animal feed; improved nutritional quality of animal feed; improved ruminant performance; improved feed digestion and absorption; preservation of high quality fodder.

3. Cellulase in Textile Industry

In some embodiments, the enzyme compositions of the present technology can be applied in the textile industry. For example, biostoning of jeans; biopolishing of textile fibers; improved fabrics quality; improved absorbance property of fibers; softening of garments; improved stability of cellulosic fabrics; removal of excess dye from fabrics; restoration of colour brightness.

4. Others Applications Using Cellulase

In some embodiments, the enzyme compositions of the present technology, wherein the enzyme is cellulase, can be used in one of the following: improved carotenoids extraction; improved oxidation and colour stability of carotenoids; improved olive oil extraction; improved malaxation of olive paste; improved quality of olive oil; reduced risk of biomass waste; production of hybrid molecules; production of designer cellulosomes.

L. Exemplary Applications Using Xylanase

In some embodiments of the present technology, enzyme compositions comprising xylanase are used. Exemplary uses include, but are not limited to bioleaching of wood pulp, treating animal feed to increase digestibility, processing food to increase clarification and converting lignocellulosic substances to feedstock and fuels.

1. Bioleaching

In some embodiments, the enzyme compositions of the present technology can be applied in bioleaching. Conventional bleaching of chemical pulp to a higher brightness without complete removal of lignin has not been successful. Conventionally, chlorine is used for bleaching. Accordingly, compositions of the present technology including xylanase are useful for bio-bleach.

2. Others Exemplary Applications Using Xylanase

Additional areas in which the present technology comprising xylanase is useful include, but are not limited to, use as food additives for poultry, in wheat flour for improving dough handling and quality of baked products, for the extraction of coffee, plant oils, and starch, in the improvement of nutritional properties of agricultural silage and grain feed, and in combination with pectinase and cellulase compositions for clarification of fruit juices and degumming of plant fiber sources such as flax, hemp, jute, and ramie.

M. Exemplary Applications Using Pectinase

In some embodiments, pectinase enzyme compositions of the present technology are useful in the fruit and textile industries. Pectinase enzyme compositions of the present technology break down complex polysaccharides of plant tissues into simpler molecules like galacturonic acids. In some embodiments, acidic pectinases enzyme compositions of the present technology are useful to bring down the cloudiness and bitterness of fruit juices. In some embodiments, acidic pectinases enzyme compositions of the present technology are useful in the textile industry for the retting and degumming of fiber crops, production of good quality paper, fermentation of coffee and tea, oil extractions and treatment of pectic waste water.

Pectate lyase is an alkaline enzyme. In some embodiments, pectate lyase enzyme compositions of the present technology are useful in the degumming and retting of fiber crops and pretreatment of pectic wastewater from fruit juice industries. Typically, these enzymes come mostly from bacterial sources. In the industrial sector, alkaline pectinase compositions of the present disclosure, mainly from *Bacillus* sp. are applied for the following purposes.

1. Retting and Degumming of Fiber Crops

In some embodiments, the enzyme compositions of the present technology are used in retting and degumming of fiber crops. For example, pectinolytic enzymes are involved in the retting and degumming of jute, flax, hemp, ramie, kenaf (*Hibiscus sativa*) and coir from coconut husks. Retting is a fermentation process in which certain bacteria (for example, *Clostridium, Bacillus*) and certain fungi (for example, *Aspergillus, Penicillium*) decompose the pectin of the bark and release fiber.

Ramie fibers are an excellent natural textile, but decorticated ramie fibers contain 20±35% ramie gum, which mainly consists of pectin and hemicellulose; hence it is necessary to degum fibers for meeting the requirement for textiles.

2. Oil Extraction

In some embodiments, the enzyme compositions of the present technology are used in oil extraction. Oils from rape seed (canola), coconut germ, sunflower seed, palm, kernel and olives are traditionally produced by extraction with organic solvents. The most commonly used solvent is hexane, which is a potential carcinogen. Cell-wall-degrading enzymes, including pectinase, may be used to extract vegetable oil in an aqueous process by liquefying the structural cell wall components of the oil-containing crop.

EXAMPLES

The present invention is further illustrated by the following examples, which should not be construed as limiting in any way.

Example 1

Entrapment of Enzymes in Carbon Nanotubes Enhances Enzyme Kinetics at Low and High Temperatures Isolated bacterial enzymes were entrapped in lipid-functionalized SWCNT. The entrapped enzymes' kinetics were tested and compared to un-trapped enzymes' kinetics at 4° C., 30° C., and 80° C.

Methods and Materials

The SWCNT, $Cu_2O$ and hydroxyapatite (HAp) nanoparticles were purchased from SIGMA-ALDRICH (Accession no: 678945, 702153 respectively).

Isolation of Industrial Enzymes Secreted from Bacteria from Soil

Pectinolytic, laccase secreting, cellulolytic, and xylanase secreting bacteria were isolated from Himalayan forest soil, which was 3800 meters above sea level. Proteolytic bacteria were isolated from forest soil.

Pectinolytic bacterial strain was isolated by the "Ruthenium red" method. In this method, several bacterial colonies were formed on YP agar plates. The YP plates were flooded by ruthenium red solution. Those colonies that showed a halo were identified as Pectinolytic strain.

Laccase secreting bacterial strain was isolated by the "Syringaldazine" method. Bacterial colonies were formed on LA plates, which were flooded by Syringaldazine solution. Those bacterial colonies that formed purple coloration were identified as laccase secreting bacteria.

Proteolytic bacterial strain was isolated by the "Casein" method. Bacterial colonies were grown on agar-azo-casein plates. Colonies that showed a white zone of precipitation, indicative of casein breakdown, were identified as proteolytic bacterial strains.

Xylanase secreting bacterial strain was isolated by the "Congo red" method. Bacterial colonies were grown on xylan-agar plates. Bacterial colonies that formed on the xylan-agar plates were flooded with congo-red solution. Those bacterial colonies that formed a halo were identified as xylanase secreting bacteria.

Cellulolytic bacterial strain was isolated by the Congo red method. Bacterial colonies were grown on CMC-agar plates. Bacterial colonies, formed on the CMC-agar plate were flooded by congo-red solution. Those bacterial colonies formed halo were identified as xylanase secreting bacteria.

The bacterial cultures were incubated at 20° C. except the proteolytic bacteria, which was incubated at 37° C.

Partial Purification of Enzymes

Pectinase enzyme was partially purified by two consecutive processes. First by ion exchange chromatography (CM Sepharose) and then followed by gel filtration chromatography (Sephadex G-75).

Laccase enzyme was partially purified by three consecutive processes. First by 30-80% ammonium sulphate cut method, followed by ion exchange chromatography (CM Sepharose), and finally by gel filtration chromatography (Sephadex G-75).

Protease enzyme was purified by three consecutive processes. First by 30-80% ammonium sulphate cut method, followed by ion exchange chromatography (CM Sepharose), and finally by gel filtration chromatography (Sephadex G-50).

Cellulase enzyme was partially purified by two consecutive processes. First by ion exchange chromatography (DEAE cellulose) and then followed by gel filtration chromatography (Sephadex G-100).

Xylanase enzyme was partially purified by two consecutive processes. First by ion exchange chromatography (CM Sepharose) and then followed by gel filtration chromatography (Sephadex G-50).

Measurement of Enzyme Activity

Pectinase from bacteria was incubated with Poly-galactouronic acid (PGA) in 25 mM Tris-HCl buffer (pH-8.5) for 2 hours at 20° C. by TBA method. After two hours of incubation the red color formation was measured at 550 nm.

The laccase activity was determined by Syringaldazine assay, which measures absorbance at 525 nm. The appropriate dilution of 1 ml supernatant was added into 3 ml of 25 mM Tris-HCl buffer, with a of pH 8.5, and a 2 ml substrate Syringaldazine solution (methanol and 1:2 dilution by Dioxan) was added to make the total assay system to 5 ml. The immediate color change from straw yellow to dark pink or violet confirms the laccase activity. This assay was done at 20° C.

Protease activity was assayed by the azo-casein method. Protease was incubated 1% (w/v) azo-casein for 10 minutes at 37° C. in 25 mM Tris-HCl buffer of pH 8.5. The reaction was stopped by addition of 4 ml of 5% trichloroacetic acid. The contents were centrifuged at 3000×g for 10 min. One milliliter supernatant was taken, and the products were measured by adding 5 ml of 0.4 M $Na_2CO_3$, followed by addition of 0.5 ml Folins Ciocalteus reagent. The optical density of samples was taken at 660 nm.

Cellulase assay was performed by dinitrosalicylic acid method. 1 ml of culture filtrate was taken in a test tube and it was equalized with 2 ml of distilled water. To the prepared culture filtrate, 3 ml of DNS reagent was added. The contents in the test tubes were heated in a boiling water bath for 5 min. After heating, the contents were allowed to cool at room temperature. At the time of cooling, 7 ml of freshly prepared 40% sodium potassium tartarate solution was added. After cooling, the samples were read at 510 nm in a U.V. spectrophotometer. The amount of reducing sugar was determined using a standard graph.

Xylanase activity was assayed using 1% solution of Birchwood xylan as the substrate and the amount of reducing sugars released was determined by the dinitrosalicylic acid method. One unit of enzyme activity was defined as 1 mM xylose equivalent produced per minute under the given conditions. The samples were read at 410 nm in a U.V. spectrophotometer.

Trapping Enzymes Inside the SWCNT

Figure 17:
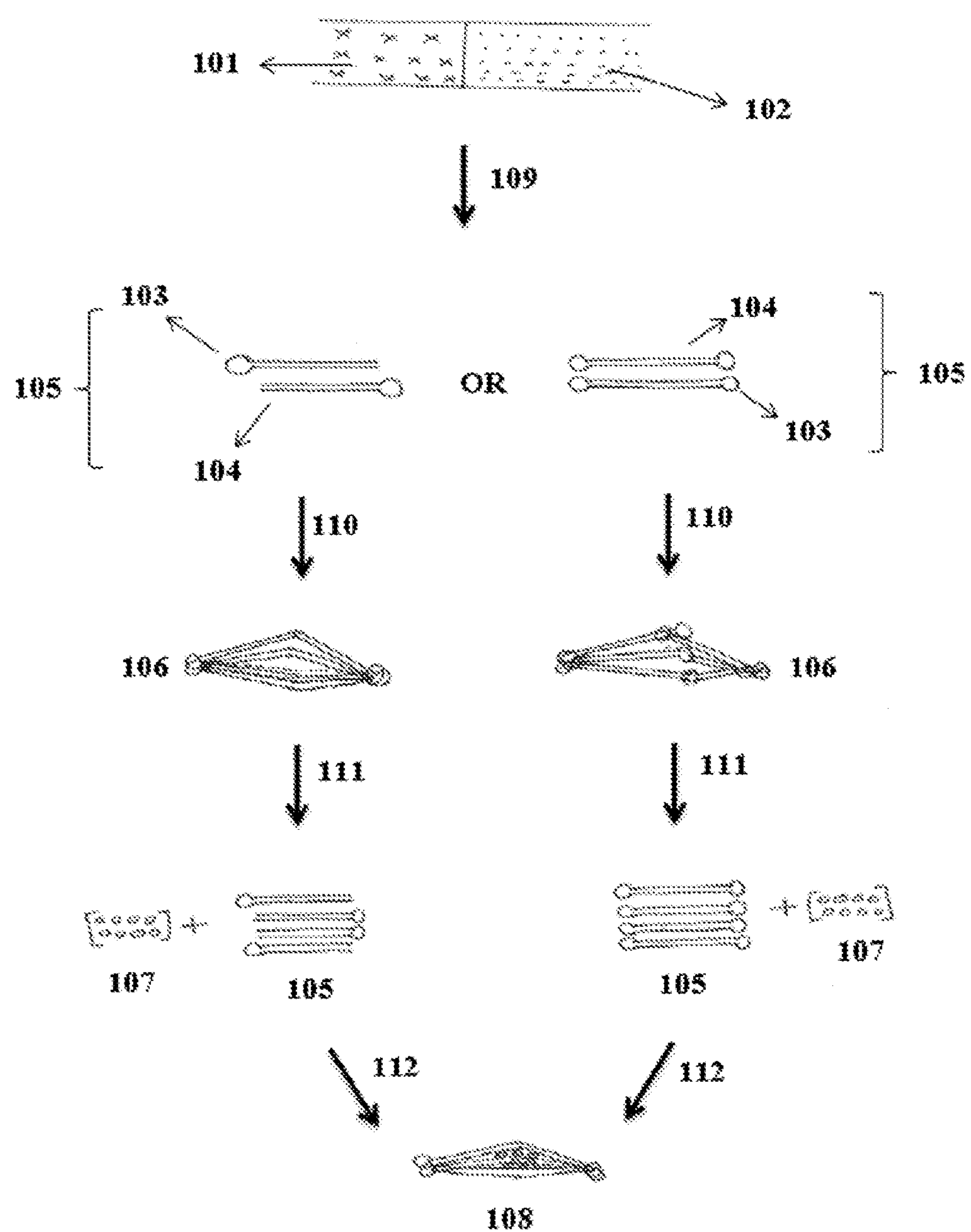
FIG. 17 is a schematic representation of the entrapment of enzymes by SWCNT.

Referring to FIG. 17, the following is a sample method for entrapping enzymes in lipid-functionalized SWCNT 100.

First a plurality of SWCNT 101 is mixed with lipids 102. The lipid to SWCNT ratio (wt/wt) is about 5:1. The basic functionalization chemistry is known in the art, see e.g., Bhattacharyya et al., Nanotechnology, 23 (2012) 385304 (8 pp) or IPO 592/KOL/2012 and PCT/IB2012/001509. Briefly, two nano-surfaces are allowed to interact in a close capillary. According to solid state interaction, the interface will diffuse only if the reaction occurs at the interface region. A molecular re-orientation is expected at the interface. Such re-orientation can be considered as a nano-scale reaction that would be coupled to a diffusive or translocation mechanism, like a solid state chemical reaction.

The linking of the lipid to the SWCNT 109 creates SWCNT with polar heads 103 and tails 104. The lipid-functionalized SWCNT 105 can have polar heads attached to one end of the SWCNT or both ends of the SWCNT.

The lipid-functionalized SWCNT will self-assemble 110 into "nano-cages" 106.

The nano-cages are mixed with enzymes 107, and the mixture is sonicated 111 for about 2-5 minutes. The amounts of lipid-functionalized SWCNT to enzyme for the experiments below were 0.5 mg/ml of SWCNT to: 0.18 mg/ml pectate lyase, 0.25 mg/ml laccase, 0.11 mg/ml cellulase, 0.2 mg/ml xylanase, and 0.22 mg/ml protease.

The sonication breaks the nano-cages 106 into individual lipid-functionalized SWCNT 105, which are in solution with the enzymes 107. The lipid-functionalized SWCNT will self-re-assemble 112 after sonication. During the self-re-assembly, enzymes will become entrapped in the formed nano-cages 108.

To observe whether nanoparticles can influence the SWCNT trapped enzymes' activity, enzymes were entrapped inside the SWCNT nanorope cage with either $Cu_2O$ or HAp or both and the activity was assayed. $Cu_2O$ concentration was 0.1 mM for laccase, and the HAp concentration was 13.2 μM for xylanase, 17.6 μM for pectate lyase and 22 μM for cellulase.

Lipids were allowed to interact with SWCNT both from one end and both ends at solid state. A molecular re-orientation occurs at the interface of SWCNT and lipids. These complexes form a pseudo-micellar structure in water or buffer of interest (e.g., 1 ml of 25 mM Tris-HCl buffer (pH 8.5)). The enzymes present in 1 ml of 25 mM Tris-HCl buffer (pH 8.5) were trapped inside the inner core of the structure at 40° C. After the activities of those SWCNT trapped enzymes were determined, the complex was centrifuged at 1000 RPM for 5 minutes followed by mild sonication. The centrifugation process serves to purify the functionalized SWCNT from unfunctionalized SWCNT. The molecular assembly collapses upon sonication. The sonication was done for 2 minutes. When re-assemble was allowed in the presence of enzymes, the complex formed the same supramolecular structure (nano-cage) with enzyme entrapped in inner core of the structure at 40° C. Typically, the assembly was allowed to re-assemble for 48 hours.

Enzyme Kinetic Parameters

The use of enzymes in industrial processes often require reactions at high and low temperatures in order to improve productivity. This in turn implicates that the enzyme be tolerant at very low temperatures. The kinetic parameters (given below) were examined to gain an insight into the tolerance of the purified pectinase, laccase, protease, cellulase and partially purified xylanase to high as well as low temperature. For the study of enzyme kinetics, the buffer (25 mM Tris-HCl, pH 8.5) contained no supplementation of corresponding calcium and copper ions, only HAp and $Cu_2O$ nanoparticle were added to the corresponding assay system.

$K_m$, $V_{max}$ and Activation Energy ($E_a$)

The kinetic parameters, $K_m$, $V_{max}$, and the activation energy ($E_a$) of both HAp treated and untreated pectinase, protease, cellulose, and xylanase, and $Cu_2O$ nanoparticle treated and untreated purified laccase enzymes were calculated. The activation energy ($E_a$) was calculated for the temperature range of 4-80° C.

$K_m$ measures how effectively the enzyme binds the substrate, i.e. the affinity between enzyme and substrate. A small $K_m$ indicates a tight binding, whereas a large $K_m$ indicates a weaker binding.

$V_{max}$ measures the rate at which substrate will be converted to product once bound to its enzyme.

$E_a$ is the minimum energy needed to cause a chemical reaction.

Results

Lipid-functionalized SWCNT trapping enhances the enzyme-substrate specificity and lowers the activation energy when compared to untrapped enzymes. Referring to Tables 1-3, all enzymes entrapped in the lipid-functionalized SWCNT with nanoparticles (NP) showed a significantly higher $V_{max}$ and lower $K_m$ and $E_a$ verses their untrapped counterparts (without NP) across all temperature ranges (4° C., 30° C., and 80° C.). These results indicate that the lipid-functionalized SWCNT entrapment enhanced the entrapped enzymes activity, which allowed the enzymes to function at a high rate outside their normal temperature range.

TABLE 1

| Enzyme Kinetics at 4° C. | | | | | | | | | | |
|---|---|---|---|---|---|---|---|---|---|---|
| | Pectinase | | Laccase | | Cellulase | | Xylanase | | Protease | |
| Enzymes | Un-trapped | SWCNT + NP Treated | Un-trapped | SWCNT + NP Treated | Un-trapped | SWCNT + NP Treated | Un-trapped | SWCNT + NP Treated | Un-trapped | SWCNT + NP Treated |
| $K_m$ | 0.27 | 0.1 | 0.449 | 0.237 | 5.67 | 0.31 | 2.28 | 1.21 | 0.63 | 0.26 |
| $V_{max}$ | 23.28 | 56.6 | 19.03 | 63.7 | 13.48 | 103 | 4.13 | 21.44 | 13.87 | 65.48 |
| $E_a$ | 68.9 | 28.55 | 38.65 | 6.706 | 48.289 | 21.814 | 54.68 | 32.42 | 41.72 | 19.4 |

TABLE 2

| Enzyme Kinetics at 30° C. | | | | | | | | | | |
|---|---|---|---|---|---|---|---|---|---|---|
| | Pectinase | | Laccase | | Cellulase | | Xylanase | | Protease | |
| Enzymes | Un-trapped | SWCNT + NP Treated | Un-Trapped | SWCNT + NP Treated | Un-trapped | SWCNT + NP Treated | Un-trapped | SWCNT + NP Treated | Un-trapped | SWCNT + NP Treated |
| $K_m$ | 0.43 | 0.2 | 0.589 | 0.465 | 2.32 | 0.24 | 1.79 | 0.98 | 0.47 | 0.23 |
| $V_{max}$ | 21.45 | 57.43 | 11.03 | 40 | 17.03 | 109.22 | 8.74 | 34.71 | 7.9 | 70 |
| $E_a$ | 78.65 | 21.87 | 35.4 | 5.06 | 29.245 | 9.96 | 31.67 | 21.97 | 43.76 | 13.498 |

TABLE 3

| Enzyme Kinetics at 80° C. | | | | | | | | | | |
|---|---|---|---|---|---|---|---|---|---|---|
| | Pectinase | | Laccase | | Cellulase | | Xylanase | | Protease | |
| Enzymes | Un-trapped | SWCNT + NP Treated | Un-trapped | SWCNT + NP Treated | Un-trapped | SWCNT + NP Treated | Un-trapped | SWCNT + NP Treated | Un-trapped | SWCNT + NP Treated |
| $K_m$ | 0.31 | 0.17 | 0.589 | 0.465 | 1.24 | 0.11 | 1.35 | 0.95 | 0.47 | 0.23 |
| $V_{max}$ | 29.48 | 60 | 11.03 | 40 | 26.87 | 127 | 17.67 | 41.42 | 7.9 | 70 |
| $E_a$ | 93.436 | 58.55 | 30.428 | 2.906 | 11.899 | 6.337 | 24.18 | 11.428 | 31.172 | 14.456 |

These results show that the enzyme compositions of the present technology have enhanced enzyme kinetics at temperature ranges both higher and lower than a control enzyme. In particular, these results show that the enzyme compositions of the present technology are useful in both high and low temperature processes or reactions, as well as reactions at optimal temperatures (e.g., 30°-40° C.).

Example 2

SWCNT Trapping Enhances Thermophilic Activity as Well as Psychrophilic Activity of Enzymes Various combinations of isolated enzymes from Example 1 (pectinase, laccase, cellulose, xylanase, and protease), SWCNT, and nanoparticles (NP) were produced and their enzyme activity at 4° C. and 80° C. were measured in 25 mM Tris-HCl, pH 8.5.

The enzymes were incubated with their substrates and either 4° C. and 80° C. in the following combinations (terms in parentheses related to columns in FIG. 1-5):

1) the enzyme alone (control)

2) enzyme plus SWCNT without sonication (Nanorope)

3) enzyme plus SWCNT with sonication (SWCNT)

4) enzyme plus NP (NP)

5) enzyme plus NP and SWCNT without sonication (NP+NR)

6) enzyme plus NP and SWCNT with sonication (NP+SWCNT)

Referring to FIGS. 1-5, nanoparticle treated enzymes trapped inside the SWCNT (NP+SWCNT) showed the highest enzyme activity among all combinations of NP supplemented enzymes and non-NP supplemented enzymes, e.g., SWCNT trapped (Enz+NP)>(Enz+NP)>Enz. It was also observed that in the presence of NP, SWCNT trapped enzymes showed more activity at 4° C. and 80° C. than enzymes trapped and without NP.

In the absence of NP and SWCNT, pectinase, laccase, protease, cellulase and xylanase showed lower activity at 4° C. and 80° C. than SWCNT entrapped enzyme plus NP. It was also observed that un-sonicated SWCNT showed low activity.

These results show that entrapping psychrophilic and mesophilic enzymes with nanoparticles by carbon nanotubes enhanced the enzymatic activity of the entrapped enzymes, as compared to controls. In particular, these results show that the enzyme compositions of the present technology are useful in processes or reactions that require low temperatures, high temperatures, or a combination thereof.

Example 3

SWCNT Promotes the Reusability of Enzymes

In this experiment it was demonstrated that SWCNT trapped enzymes could be reused for about 4-5 cycles with high activity at both high and low temperature, whereas untrapped enzymes lost their activities after one use only.

Method and Materials

To observe the reusability of SWCNT trapped enzymes, the entrapped enzymes were sonicated for 2 minutes by Bransonic® ultrasonic cleaner (Model no. 1510E-MTH) with output power 70 W, 42 KHz+/−6%. Then the samples were centrifuged, the “old reaction” product (supernatant) was removed, new buffer (1 ml of 25 mM Tris-HCl, pH 8.5) was added and the enzymes and nanotubes were allowed to self-assemble. Typically the assembly was allowed to re-assemble for 48 hours, at a temperature 40° C., followed by centrifugation at 1000 RPM for 5 minutes. After re-assembly, substrate was added as described in Example 1, and enzyme activity was assayed. This entire experiment was carried out for 5-6 times to demonstrate the reusability of SWCNT trapped enzyme system.

The molecular assembly was sonicated. The sonication was done for 2 minutes. The complex was then centrifuged at 1000 RPM for 5 minutes. The centrifugation process serves to purify functionalized SWCNT from un-functionalized SWCNT. When the SWCNT are allowed to re-assemble in presence of enzymes, the complex forms the same supramolecular structure (nanorope) with enzyme entrapped in inner core of the structure at 4° C. 1 ml of 25 mM Tris-HCl buffer (pH 8.5) was used in this experiment.

Results

Figure 6:
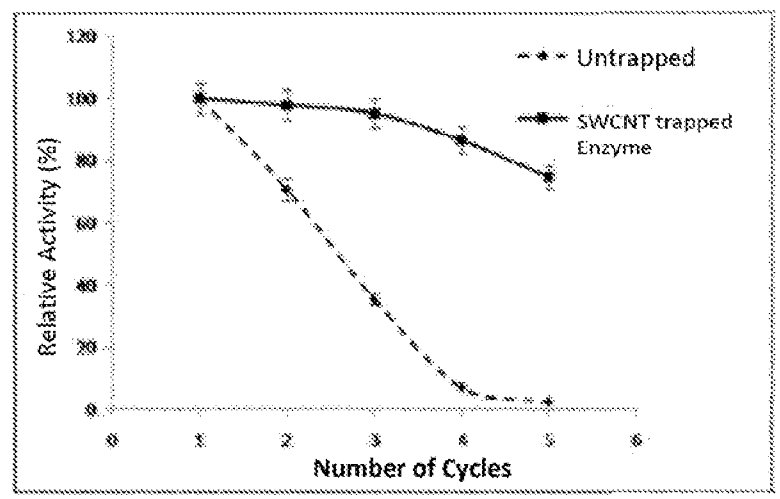
FIGS. 6A and 6B are graphs comparing the enzymatic activity of SWCNT trapped and untrapped pectinase, 4° C. and 80° C., respectively.
Figure 6:
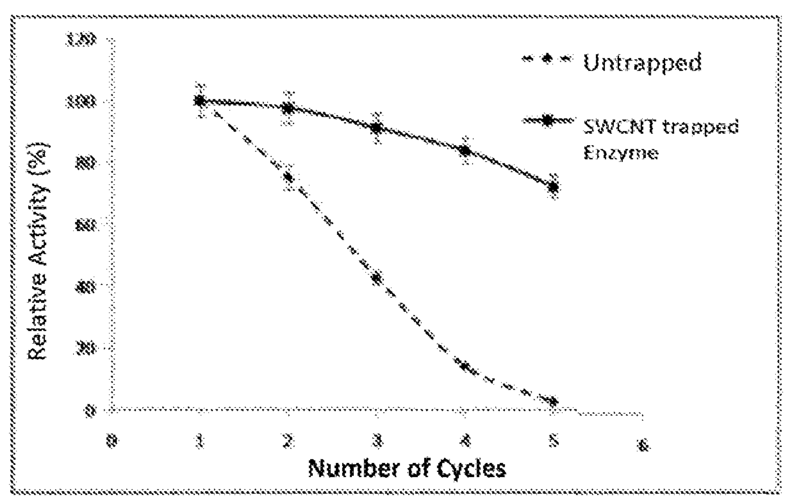
Figure 7A:
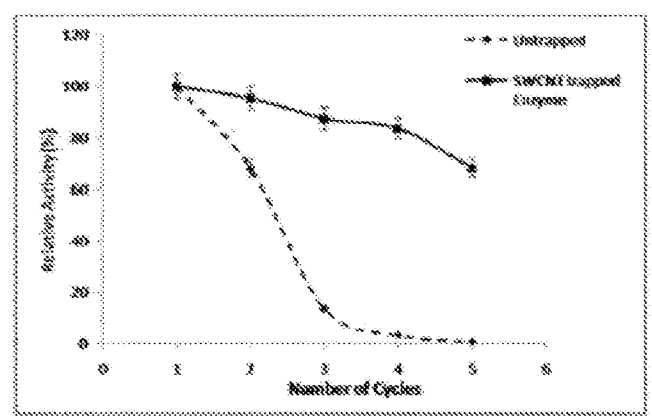
FIGS. 7A and 7B are graphs comparing the enzymatic activity of laccase that is either SWCNT trapped or untrapped after multiple cycles of use, at 4° C. and 80° C., respectively.
Figure 7B:
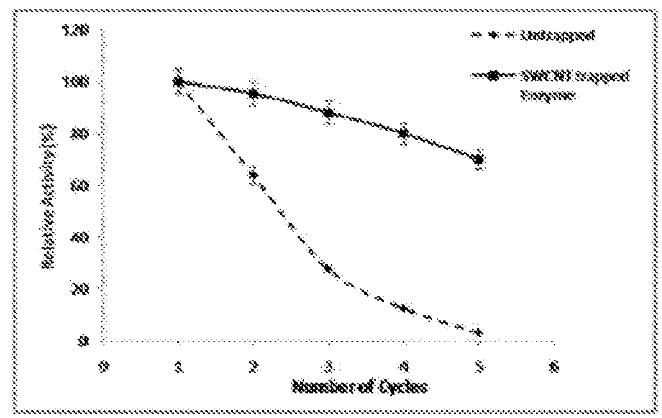
Figure 8:
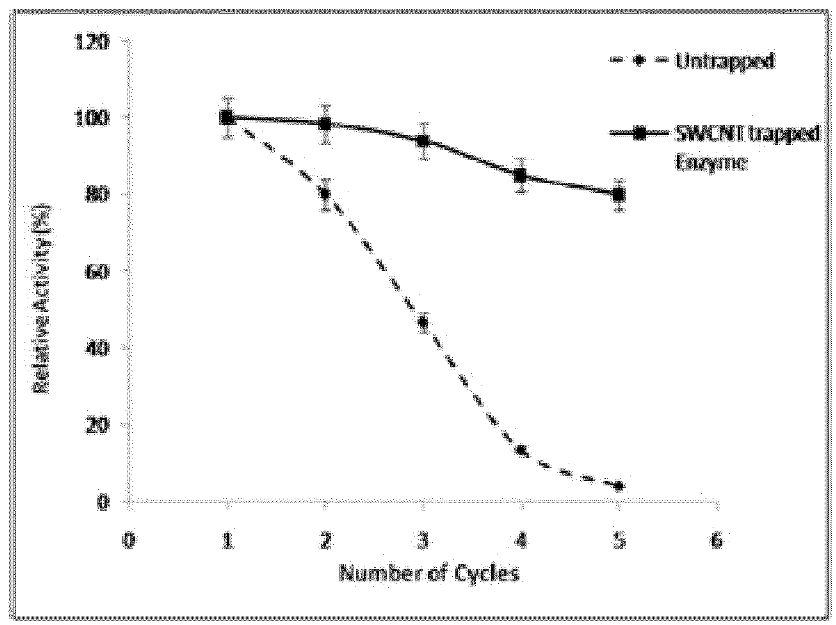
FIGS. 8A and 8B are graphs comparing the enzymatic activity of protease that is either SWCNT trapped or untrapped after multiple cycles of use, at 4° C. and 80° C., respectively.
Figure 8:
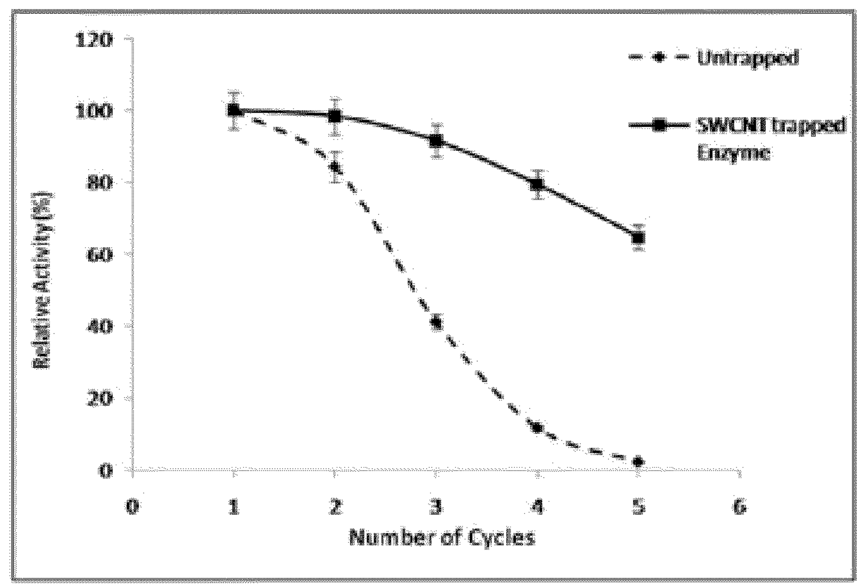
Figure 9A:
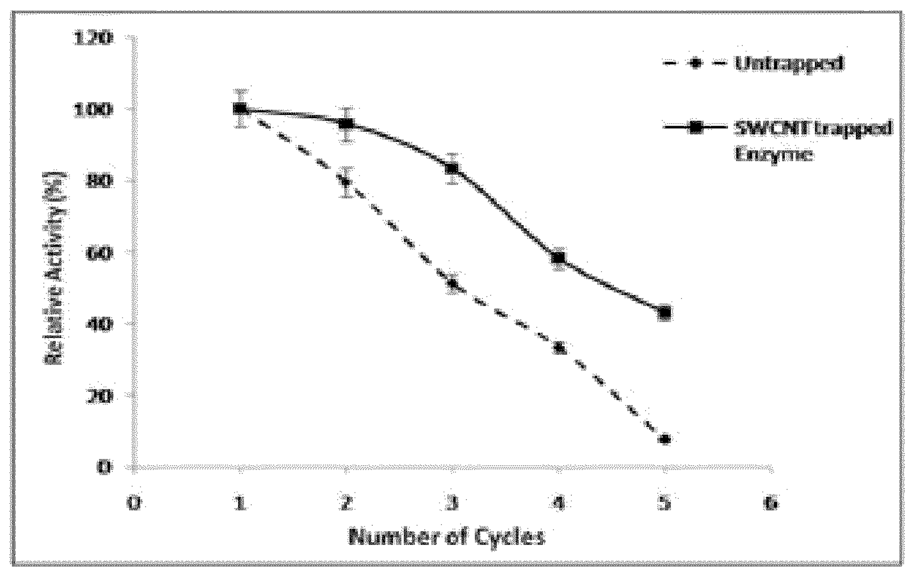
FIGS. 9A and 9B are graphs comparing the enzymatic activity of cellulase that is either SWCNT trapped or untrapped after multiple cycles of use, at 4° C. and 80° C., respectively.
Figure 9B:
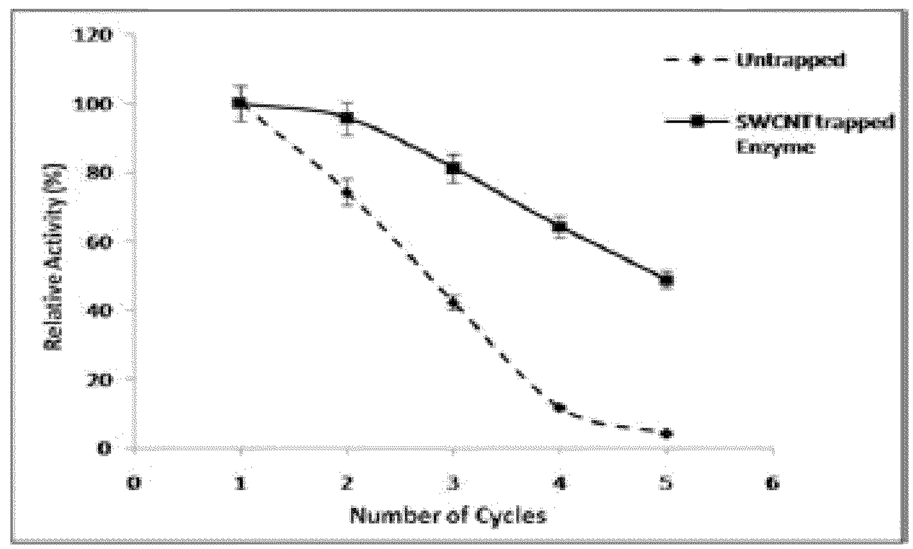
Figure 10A:
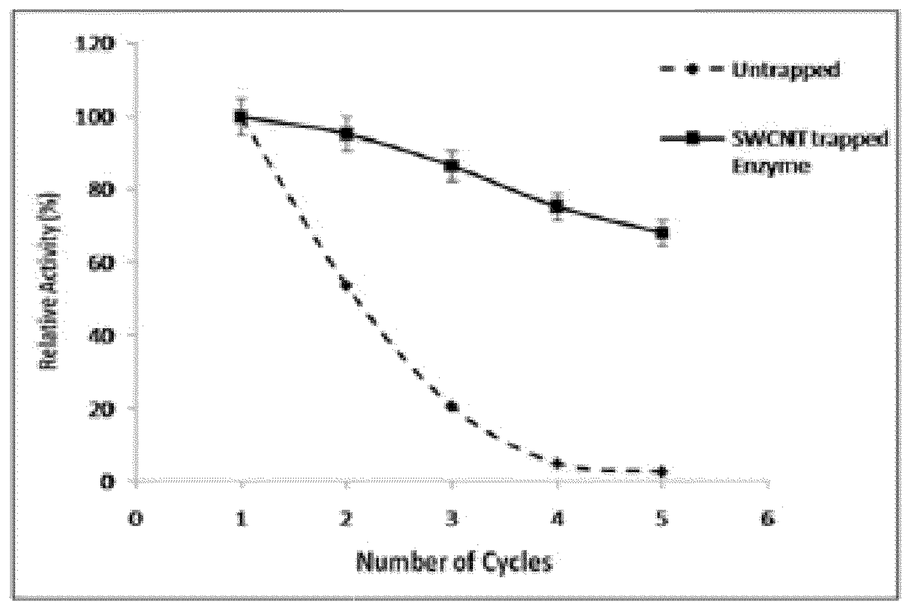
FIGS. 10A and 10B are graphs comparing the enzymatic activity of xylanase that is either SWCNT trapped or untrapped after multiple cycles of use, at 4° C. and 80° C., respectively.
Figure 10B:
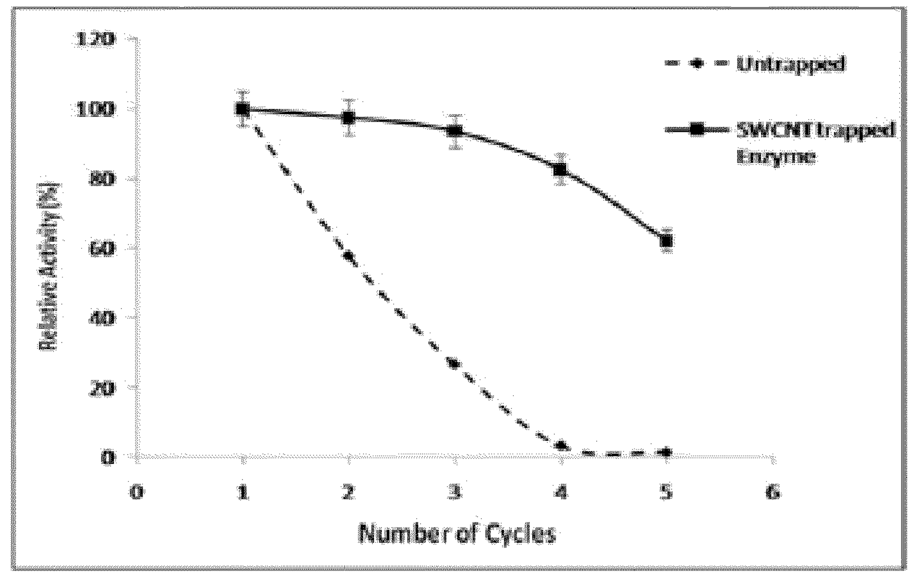

SWCNT trapped pectinase retained 75% and 72% of its enzymatic activity in the 5th cycle at 4° C. and 80° C., respectively. FIG. 6. SWCNT trapped laccase retained 68% and 70% of its enzymatic activity in the 5th cycle at 4° C. and 80° C., respectively. FIG. 7. SWCNT trapped protease retained its 80% of its enzymatic activity in the 4th cycle at both 4° C. and 80° C. FIG. 8. SWCNT trapped cellulase retained 60% and 65% of its enzymatic activity in the 4th cycle at 4° C. and 80° C., respectively. FIG. 9. SWCNT trapped Xylanase 70% and 63% of its enzymatic activity in the 5th cycle at 4° C. and 80° C., respectively. FIG. 10.

These results show that the enzyme compositions of the present technology are reusable and can be used in many reactions (e.g., serially) as compared to a control enzyme. In particular, these results show that the enzyme compositions of the present technology are useful, efficient, reusable, and provide cost-savings.

Example 4

SWCNT Trapping Promotes Retention of Enzyme Activity at High and Low Temperature The uses of enzymes in industrial processes often require reactions for a long time span in order to improve productivity. To measure the time kinetics, SWCNT trapped pectinase was incubated for 30-300 minutes, SWCNT trapped laccase was incubated for 5-120 minutes, SWCNT trapped protease was incubated for 30-180 minutes, SWCNT trapped cellulase was incubated for 1-5 hours and xylanase was incubated for 30-180 minutes at both 4° C. and 80° C. As a control, the time kinetics was measured for enzyme in the absence of SWCNT entrapment.

Figure 11A:
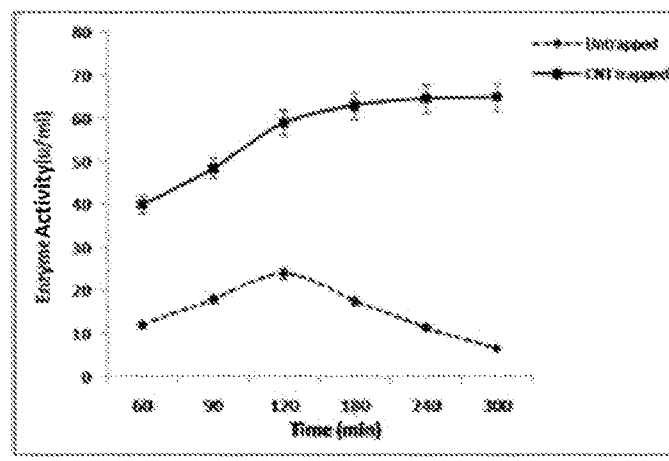
FIGS. 11A and 11B are graphs comparing the time kinetics of enzymatic activity of pectinase in SWCNT trapped and untrapped conditions, at 4° C. and 80° C., respectively.
Figure 11B:
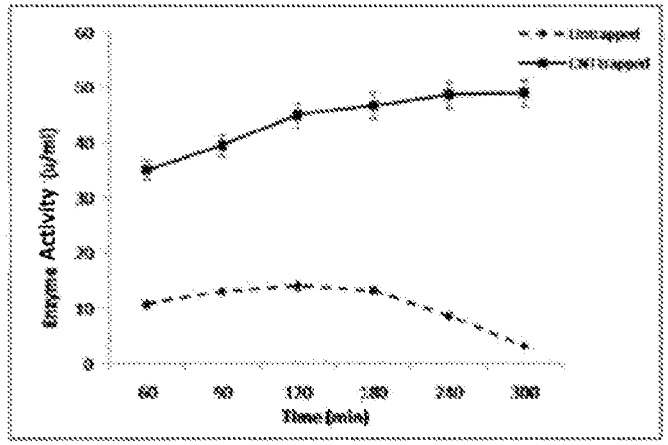
Figure 12A:
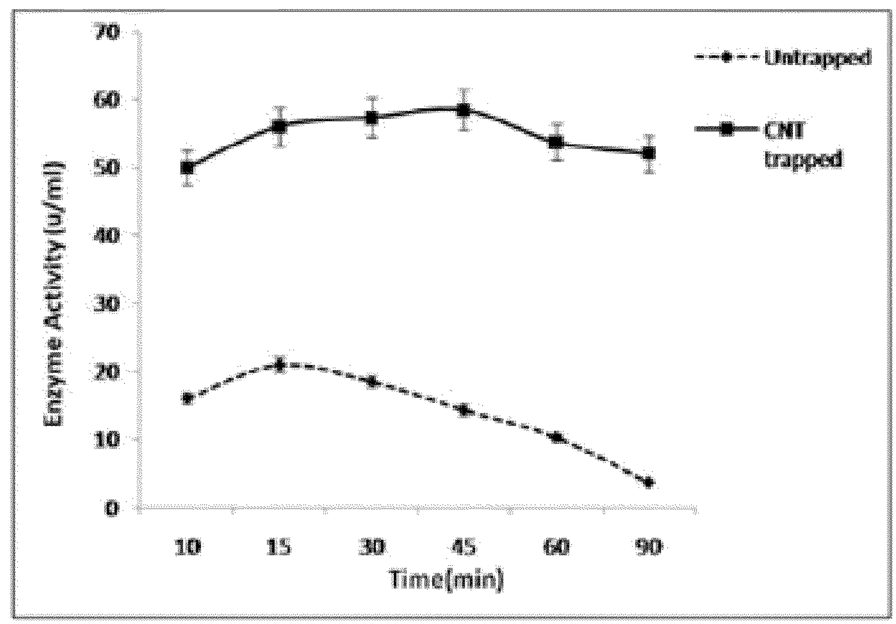
FIGS. 12A and 12B are graphs comparing the time kinetics of enzymatic activity of laccase trapped in SWCNT or untrapped, at 4° C. and 80° C., respectively.
Figure 12B:
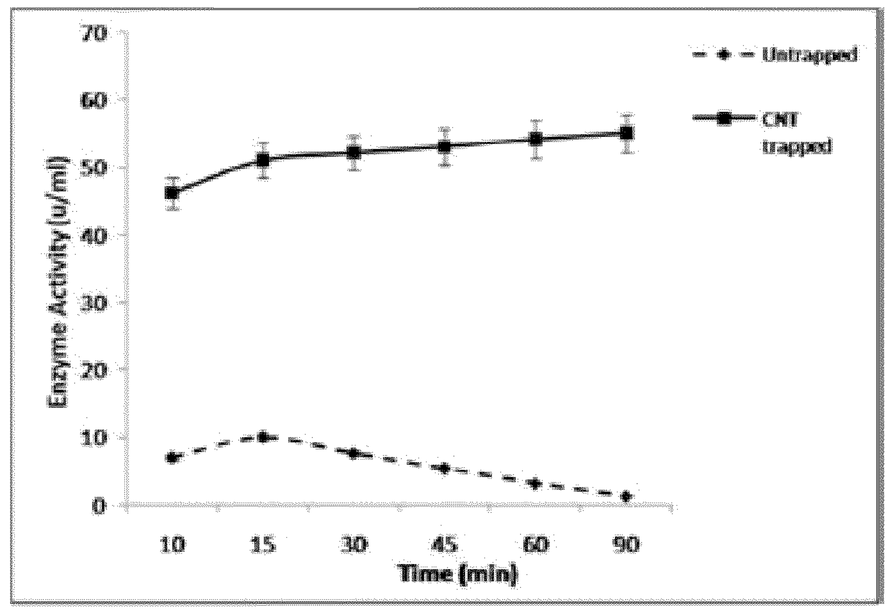
Figure 13:
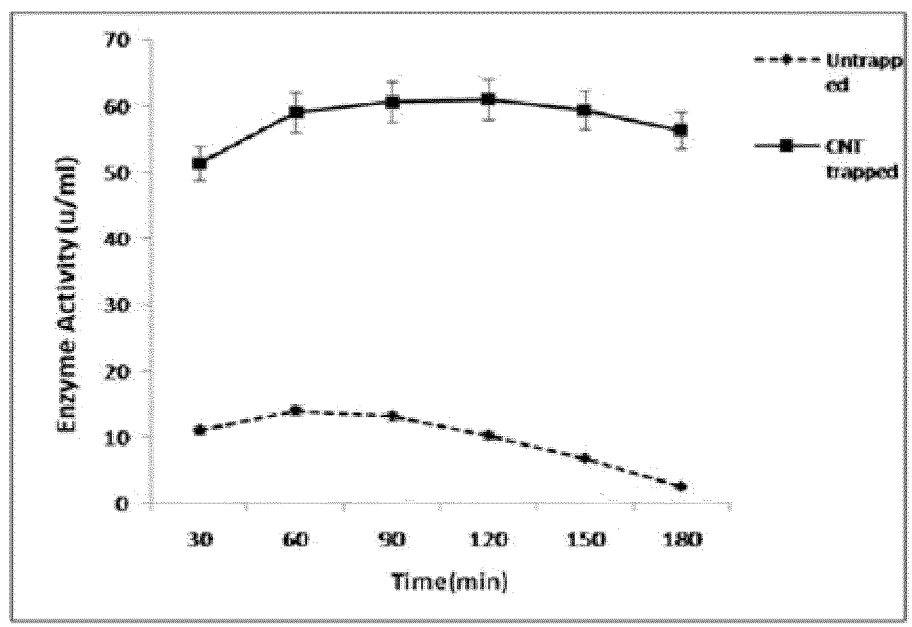
FIGS. 13A and 13B are graphs comparing the time kinetics of enzymatic activity of protease trapped in SWCNT or untrapped, at 4° C. and 80° C., respectively.
Figure 13:
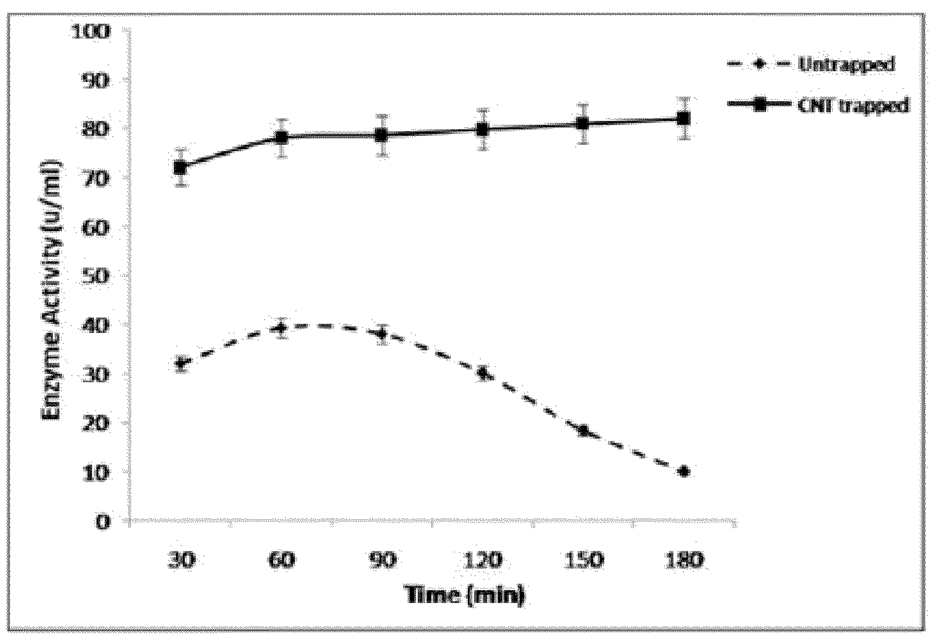
Figure 14:
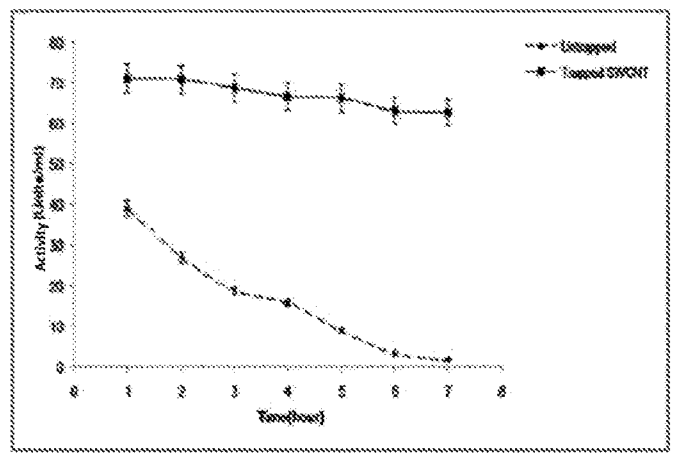
FIGS. 14A and 14B are graphs comparing the time kinetics of enzymatic activity of cellulase trapped in SWCNT or untrapped, at 4° C. and 80° C., respectively.
Figure 14:
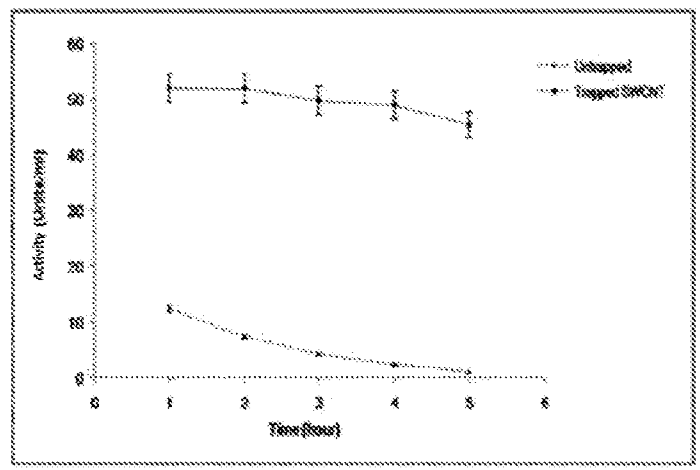
Figure 15:
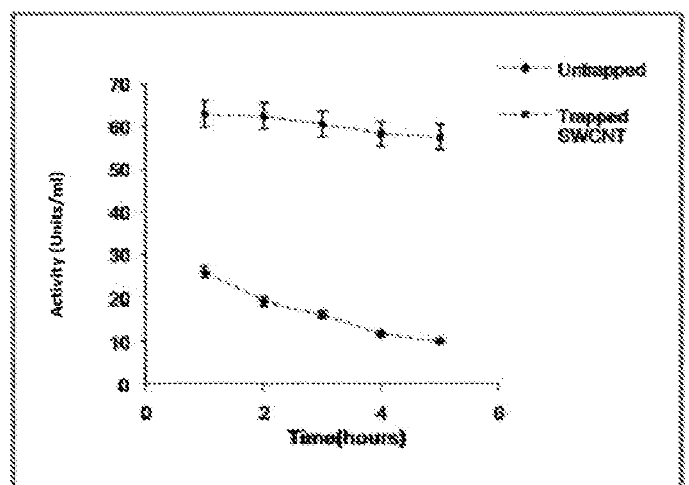
FIGS. 15A and 15B are graphs comparing the time kinetics of enzymatic activity of xylanase trapped in SWCNT or untrapped, at 4° C. and 80° C., respectively.
Figure 15:
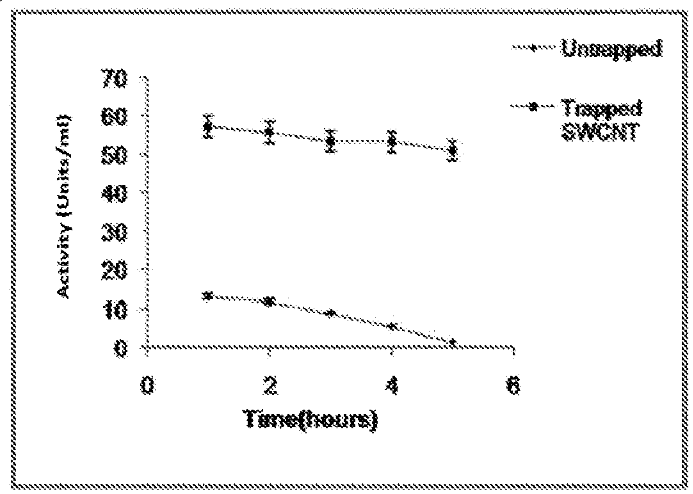

The alteration in enzyme activity with time, in the presence and absence of SWCNT entrapment was monitored by studying time kinetics. It was observed that pectinase retained its activity for 2 hours at its optimum temperature, after which the enzymatic activity decreased with time. However, SWCNT trapped pectinase retained enzymatic activity for 4-5 hours at 4° C., as well as at 80° C. FIG. 11. Untrapped laccase retained its enzymatic activity for 15 minutes at its optimum temperature; whereas SWCNT trapped laccase retained its enzymatic activity for 90 minutes at 4° C., as well as at 80° C. FIG. 12. Similarly, untrapped protease showed enzymatic activity for 1 hour at optimum temperature, whereas SWCNT trapped protease retained enzymatic activity for 3 hours at both 4° C. and 80° C. FIG. 13. Untrapped cellulose retained its enzymatic activity at its optimum temperature for 1 hour; whereas SWCNT trapped cellulase retained its enzymatic activity for 4-5 hours at 4° C. and 80° C. FIG. 14. Untrapped xylanase retained its enzymatic activity at its optimum temperature for 1 hour; whereas SWCNT trapped xylanase retained its enzymatic activity for 4-5 hours at 4° C. and 80° C. FIG. 15.

These results show that the enzyme compositions of the present technology have enhanced duration of enzyme activity at higher and lower temperatures as compared to a control enzyme. In particular, these results show that the enzyme compositions of the present technology are useful in improving efficiency and productivity in processes or reactions.

Example 5

Study of Psychrophilic Enzyme Stability by Freeze-Thaw Experiments

This study was performed to demonstrate that psychrophilic enzyme entrapped lipid-functionalized carbon nanotubes retain enzymatic activity after many cycles of freeze-thaw cycles.

The enzymes in the freeze thaw experiments were either SWCNT trapped enzymes or untrapped enzymes. Enzyme activity assays were performed for both trapped and untrapped enzymes with repeated cycles of freezing and thawing over a length of time until the control enzyme activity declined drastically or was completely lost.

Figure 16:
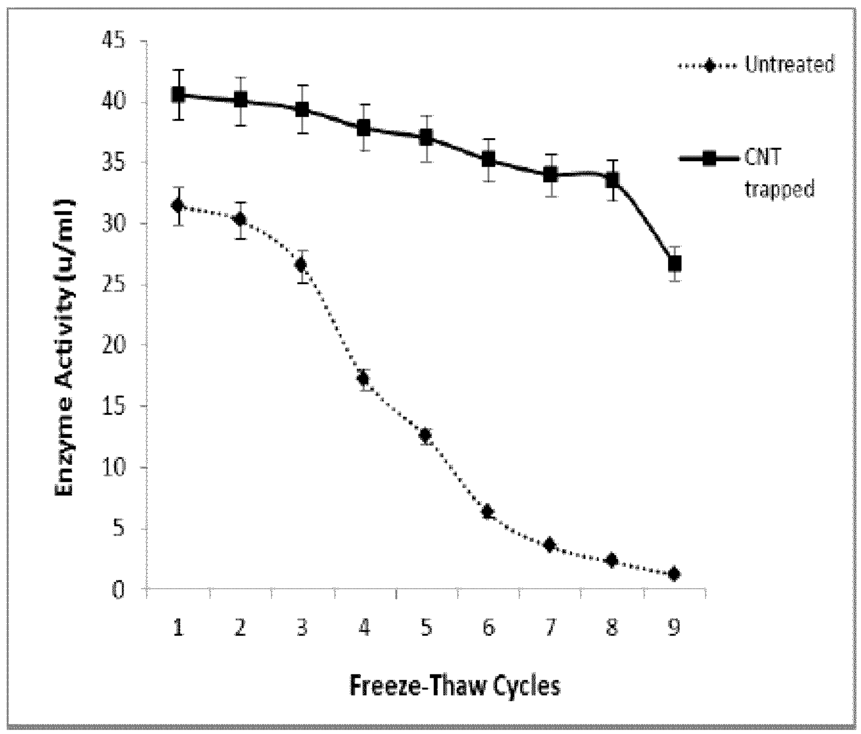
FIGS. 16(A-E) are graphs comparing the enzymatic activity of SWCNT trapped or untrapped enzymes after freeze-thaw cycles of the enzymes. The enzymes are represented as follows: (A) pectinase; (B) laccase; (C) protease; (D) cellulase; and (E) xylanase.
Figure 16:
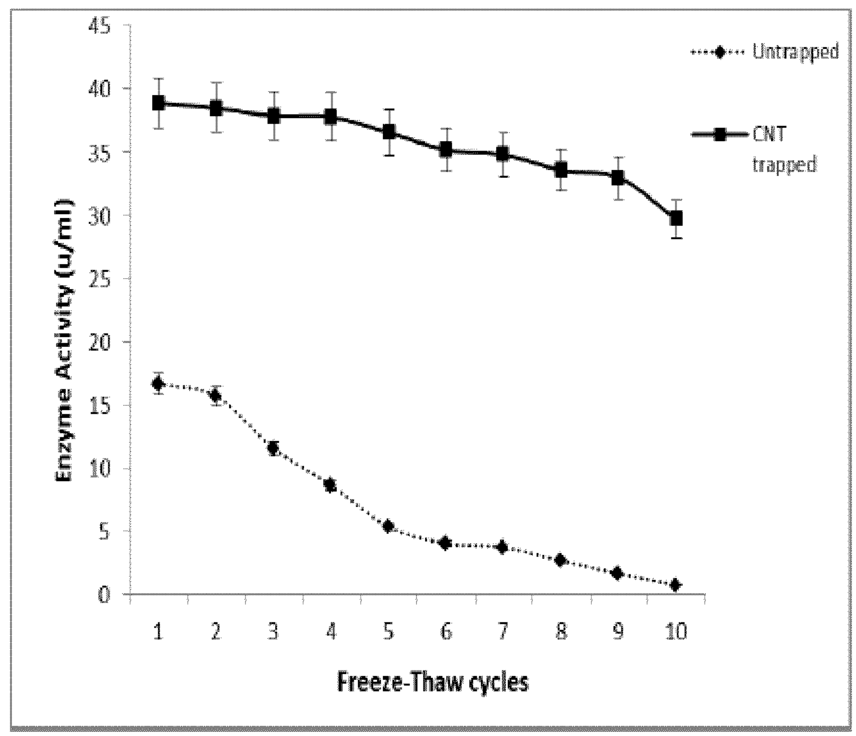
Figure 16:
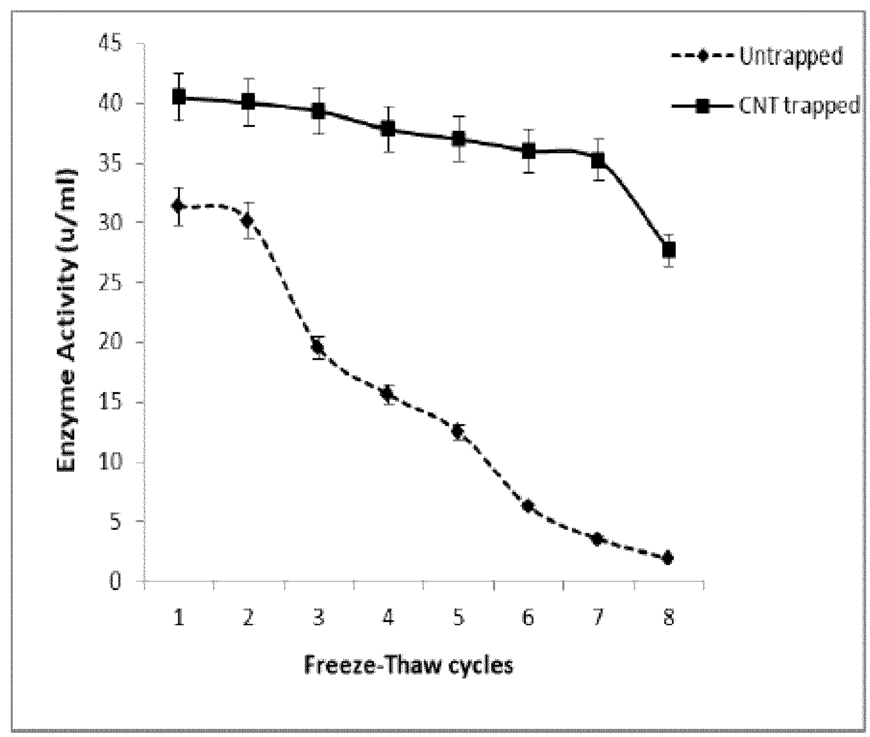
Figure 16:
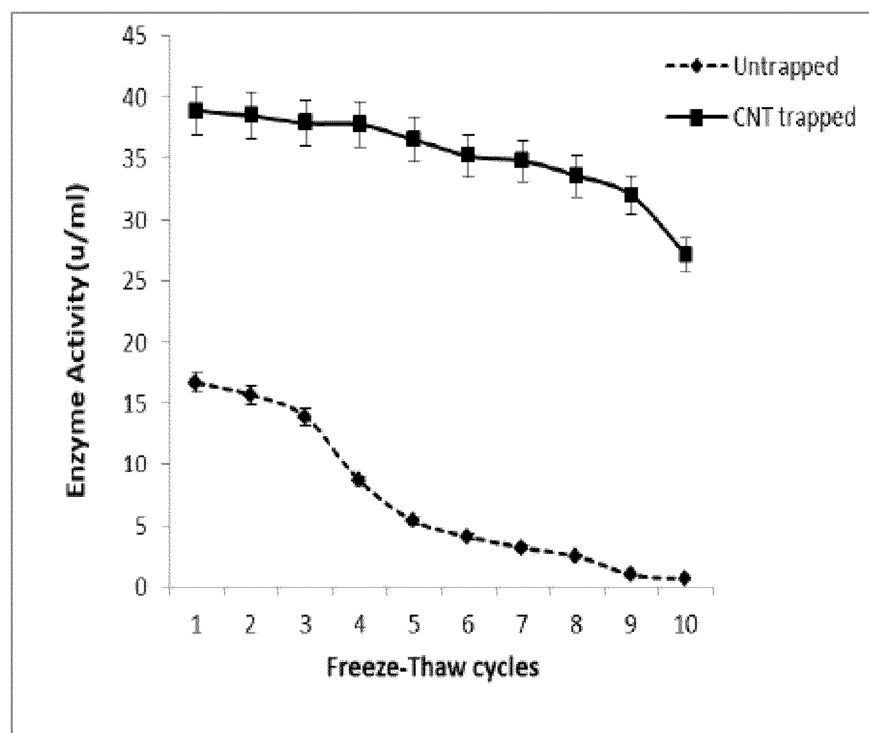
Figure 16:
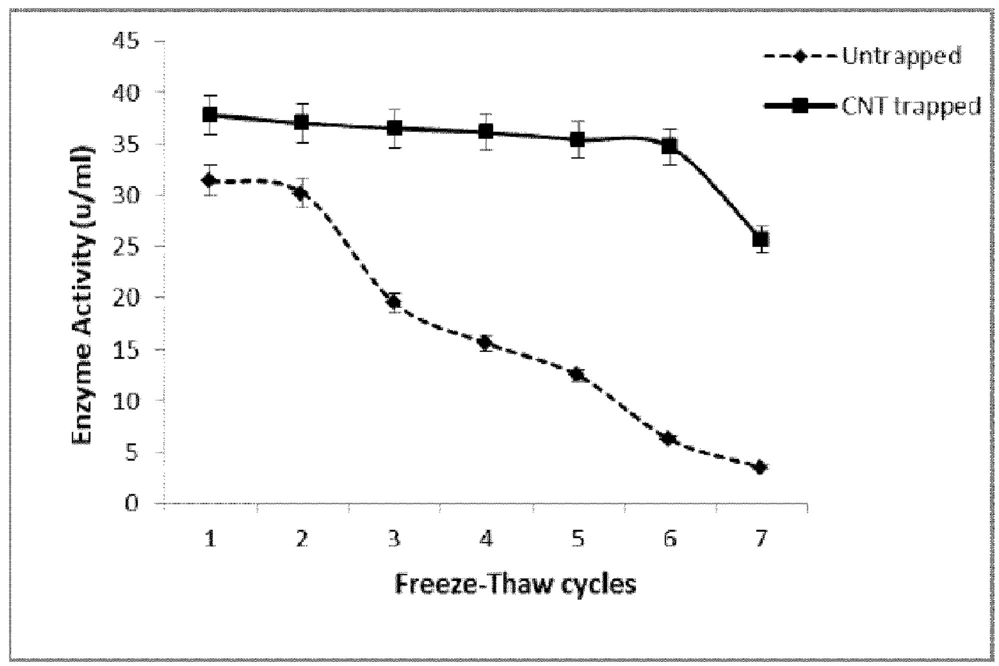

Untrapped pectinase retained its enzymatic activity for 2-3 freeze-thaw cycles, after three cycles its activity decreased drastically. FIG. 16A. In contrast, SWCNT trapped pectinase enzymatic activity remained for the 7 freeze-thaw cycles performed in this experiment. FIG. 16A. SWCNT trapping also helped purified laccase to retain its enzymatic activity for the 10 freeze-thaw cycles (when the test was ended), whereas untrapped laccase remained enzymatically active for only 2 freeze-thaw cycles. FIG. 16B. Untrapped protease retained its enzymatic activity for 2-3 freeze-thaw cycles, whereas SWCNT trapped protease retained much higher enzyme activity for the 8 freeze-thaw cycles performed in the experiment. FIG. 16C. Untrapped protease retained its enzymatic activity for about three freeze-thaw cycles, whereas SWCNT trapped protease retained its enzymatic activity for the 10 freeze-thaw cycles performed in the experiment. FIG. 16D. Untrapped xylanase retained its enzymatic activity for two freeze-thaw cycles. FIG. 16E. In contrast, SWCNT trapped xylanase retained much higher enzymatic activity for the 7 freeze-thaw cycles performed in the experiment. FIG. 16E.

These results show that the enzyme compositions of the present technology maintain high enzymatic activity after many freeze-thaw cycles as compared to a control enzyme. In particular, these results show that the enzyme compositions of the present technology are useful for the storage of enzymes for repeated future use without appreciable loss of activity.

Example 6

SWCNT Trapping Increases the Half-Life and Lowers the Decay Constant of all Five Enzymes Tested, with Decreasing as Well as Increasing Temperatures To observe thermal stability, $Cu_2O$ nanoparticle treated purified laccase trapped inside SWCNT and un-trapped laccase enzymes were subjected to temperatures of 4° C. to 20° C. (277-293 K) and 40-80° C. (313-353K) for up to 10 minutes. Inactivation parameters comprising half-life ($t_{1/2}$), decay rate constant (k), and deactivation energy (Ed) were calculated for this study. For purified pectinase, protease, cellulase and partially purified xylanase, a similar protocol was followed to observe the thermal stability; the difference was that HAp NPs were used. The PGA, azo-casein, CMC, and Birchwood xylan (substrates for pectinase, protease, cellulase, and xylanase, respectively) concentrations were 0.75% and syringaldazine (substrate for laccase) concentration used was 1 mM.

A semi-logarithmic plot of residual activity versus time (at 4-20° C.) and (at 40-80° C.) for each cases were linear. The plots suggested that un-trapped enzymes were cold and heat inactivated with first order kinetics, but the lipid-functionalized SWCNT trapped enzymes were cold and heat activated with first order kinetics. The half-life ($t_{1/2}$) values according to the plots were calculated (Tables 4-23).

TABLE 4

| Psychrostable untrapped pectinase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.131 | 5.30 | −139.12 |
| 280 | 0.069 | 10.04 | |
| 283 | 0.074 | 9.36 | |
| 288 | 0.090 | 7.70 | |
| 293 | 0.0023 | 301.3 | |

TABLE 5

| Psychrostable SWCNT trapped pectinase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.0056 | 124.42 | 108.87 |
| 280 | 0.029 | 23.89 | |
| 283 | 0.048 | 14.43 | |
| 288 | 0.079 | 8.77 | |
| 293 | 0.150 | 4.62 | |

TABLE 6

| Thermostable untrapped pectinase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.03 | 23.1 | −35.7 |
| 333 | 0.06 | 11.55 | |
| 343 | 0.08 | 8.66 | |
| 353 | 0.11 | 6.95 | |
| 363 | 0.163 | 4.25 | |

TABLE 7

| Thermostable SWCNT trapped pectinase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.01 | 69.3 | 71.63 |
| 333 | 0.00495 | 140 | |
| 343 | 0.00230 | 301.3 | |
| 353 | 0.01450 | 477.9 | |
| 363 | 0.00028 | 2501.9 | |

TABLE 8

| Psychrostable untrapped laccase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.096 | 7.22 | −105.136 |
| 280 | 0.060 | 11.55 | |
| 283 | 0.029 | 23.89 | |
| 288 | 0.0132 | 52.50 | |
| 293 | 0.0051 | 135.88 | |

TABLE 9

| Psychrostable SWCNT trapped laccase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.0095 | 72.94 | 90.125 |
| 280 | 0.0160 | 43.31 | |
| 283 | 0.0500 | 13.86 | |
| 288 | 0.0800 | 8.66 | |
| 293 | 0.1100 | 6.30 | |

TABLE 10

| Thermostable untrapped laccase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.0132 | 52.50 | −51 |
| 333 | 0.0280 | 24.75 | |
| 343 | 0.0640 | 10.83 | |
| 353 | 0.0900 | 7.70 | |
| 363 | 0.2060 | 3.36 | |

TABLE 11

| Thermostable SWCNT trapped laccase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.01400 | 49.5 | 74.87 |
| 333 | 0.00690 | 100.4 | |
| 343 | 0.00360 | 192.5 | |
| 353 | 0.00159 | 435.8 | |
| 363 | 0.00031 | 3647.3 | |

TABLE 12

| Psychrostable untrapped protease inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.127 | 5.45 | −113.54 |
| 280 | 0.075 | 9.24 | |
| 283 | 0.043 | 16.12 | |
| 288 | 0.022 | 31.50 | |
| 293 | 0.0045 | 154 | |

TABLE 13

| Psychrostable SWCNT trapped protease inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.0035 | 198 | 122.19 |
| 280 | 0.0210 | 33 | |
| 283 | 0.0480 | 14.44 | |
| 288 | 0.0750 | 9.24 | |
| 293 | 0.1430 | 4.85 | |

TABLE 14

| Thermostable untrapped protease inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.010 | 69.30 | −43.6 |
| 333 | 0.030 | 23.10 | |
| 343 | 0.044 | 15.75 | |
| 353 | 0.055 | 12.60 | |
| 363 | 0.103 | 6.70 | |

TABLE 15

| Thermostable SWCNT trapped protease inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.02000 | 34.6 | 58.322 |
| 333 | 0.00721 | 96.12 | |
| 343 | 0.00500 | 138.60 | |
| 353 | 0.00290 | 239.80 | |
| 363 | 0.00079 | 877.30 | |

TABLE 16

| Psychrostable untrapped cellulase inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.0290 | 23.95 | −4.434 |
| 280 | 0.0250 | 27.70 | |
| 283 | 0.0220 | 32.04 | |
| 288 | 0.0195 | 35.60 | |
| 293 | 0.0182 | 38.04 | |

TABLE 17

| Psychrostable SWCNT trapped cellulase inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.00915 | 75.70 | 34.454 |
| 280 | 0.01120 | 61.80 | |
| 283 | 0.01920 | 36.08 | |
| 288 | 0.02600 | 26.49 | |
| 293 | 0.03400 | 20.25 | |

TABLE 18

| Thermostable untrapped cellulase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.085 | 8.10 | −0.889 |
| 333 | 0.070 | 9.95 | |
| 343 | 0.064 | 10.83 | |
| 353 | 0.0360 | 19.21 | |
| 363 | 0.0240 | 28.61 | |

TABLE 19

| Thermostable SWCNT trapped cellulase inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.0110 | 61.12 | 20.87 |
| 333 | 0.0270 | 54.66 | |
| 343 | 0.0130 | 52.83 | |
| 353 | 0.0142 | 48.81 | |
| 363 | 0.0220 | 32.13 | |

TABLE 20

| Psychrostable untrapped xylanase inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.038 | 18.01 | −1.436 |
| 280 | 0.033 | 21.25 | |
| 283 | 0.026 | 26.69 | |
| 288 | 0.027 | 30.61 | |
| 293 | 0.022 | 32.69 | |

TABLE 21

| Psychrostable SWCNT trapped xylanase inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 277 | 0.0130 | 54.53 | 23.168 |
| 280 | 0.0210 | 32.51 | |
| 283 | 0.0245 | 28.33 | |
| 288 | 0.0360 | 19.25 | |
| 293 | 0.0420 | 16.61 | |

TABLE 22

| Thermostable untrapped xylanase inactivation | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.046 | 15.068 | −0.189 |
| 333 | 0.045 | 15.520 | |
| 343 | 0.037 | 18.570 | |
| 353 | 0.033 | 21.200 | |
| 363 | 0.030 | 22.950 | |

TABLE 23

| Thermostable SWCNT trapped xylanase inactivation: | | | |
|---|---|---|---|
| Pre-incubation temperature(K) | Decay constant(k) ($min^{-1}$) | Half-life($t_{1/2}$) (min) | Ed ($KJmol^{-1}$) |
| 323 | 0.0190 | 37.00 | 9.537 |
| 333 | 0.0250 | 27.89 | |
| 343 | 0.0360 | 19.45 | |
| 353 | 0.0450 | 15.41 | |
| 363 | 0.0514 | 13.48 | |

These results show that the enzyme compositions of the present technology enabled the entrapped enzymes to maintain high enzymatic activity and have an increased half-life at both lower and higher temperatures than control enzymes. In particular, these results show that the psychrophilic and mesophilic enzyme compositions of the present technology can be used in processes or reactions at very high temperatures, high temperatures, low temperatures, very low temperatures, or a combination thereof.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed is:

1. An enzyme composition comprising:

one or more self-assembled lipid-functionalized graphene or lipid-functionalized fullerene nano-cages; and at least one enzyme entrapped by, but not linked to, the lipid-functionalized graphene or the lipid-functionalized fullerene nano-cage, wherein the entrapped enzyme in the composition has an enhanced activity as compared to an untrapped enzyme.

2. The composition of claim 1, wherein the entrapped enzyme comprises one or more of a laccase, a pectinase, a protease, a cellulase and a xylanase.

3. The composition of claim 1, wherein the entrapped enzyme comprises one or more of psychrophilic enzymes, mesophilic enzymes, and thermophilic enzymes.

4. The composition of claim 1, further comprising a plurality of nanoparticles, wherein the nanoparticles are in contact with, but not linked to, the enzyme.

5. The composition of claim 4, wherein the nanoparticles comprise one or more of hydroxyapatite, copper, magnesium chloride, manganese chloride, calcium chloride, zinc, magnesium, and manganese.

6. The composition of claim 1, wherein the lipid-functionalized graphene or lipid-functionalized fullerene nano-cages, comprise at least one lipid comprising one or more of a phospholipid, a sphingolipid, a phosphosphingolipid, and a steroid.

7. The composition of claim 1, wherein the lipid-functionalized fullerene comprises at least one lipid-functionalized carbon nanotube.

8. The composition of claim 7, wherein the carbon nanotube comprises one or more of single-wall carbon nanotubes (SWCNT), double-walled carbon nanotubes, or multi-walled carbon nanotubes.

9. The composition of claim 7, wherein the ratio (wt/wt) of lipid-functionalized carbon nanotubes to the enzyme is about 6:1 to about 2:1.

10. The composition of claim 7, wherein the ratio (wt/wt) of lipids to carbon nanotubes is about 5:1.

11. The composition of claim 1, wherein the entrapped enzyme comprises a recombinant enzyme.

* * * * *